United States Patent [19]
Thomas et al.

[11] Patent Number: 5,966,763
[45] Date of Patent: Oct. 19, 1999

[54] SURFACE PAD SYSTEM FOR A SURGICAL TABLE

[75] Inventors: James Milton Cherry Thomas, Mt. Pleasant; Robert C. Novack, Charleston; Karl Norman Caldwell, Summerville; John Alan Bobey, Mt. Pleasant; Marla Dukes Repik, Charleston, all of S.C.

[73] Assignee: Hill-Rom, Inc., Batesville, Ind.

[21] Appl. No.: 08/691,573

[22] Filed: Aug. 2, 1996

[51] Int. Cl.⁶ .......................... A47C 27/10; A61G 13/12
[52] U.S. Cl. ................. 5/715; 5/600; 5/421; 5/702; 5/909; 5/911; 5/713; 5/740
[58] Field of Search ..................... 5/615, 715, 600, 5/911, 909, 902, 421, 655.4, 655.5, 655.9, 740, 913

[56] References Cited

U.S. PATENT DOCUMENTS

| | | | |
|---|---|---|---|
| 1,772,318 | 8/1930 | Hart | 5/615 |
| 2,910,259 | 10/1959 | Johnson | 5/646 |
| 3,227,440 | 1/1966 | Scott | 5/618 |
| 3,451,071 | 6/1969 | Whiteley . | |
| 3,492,988 | 2/1970 | De Mare | 5/615 |
| 4,066,072 | 1/1978 | Cummins . | |
| 4,287,620 | 9/1981 | Zur | 5/615 |
| 4,483,029 | 11/1984 | Paul | 5/689 |
| 4,637,083 | 1/1987 | Goodwin | 5/689 |
| 4,879,777 | 11/1989 | Goodwin | 5/689 |
| 4,914,760 | 4/1990 | Hargest et al. | 5/689 |
| 4,926,951 | 5/1990 | Carruth et al. | 177/144 |
| 4,934,002 | 6/1990 | Watanabe | 5/715 |
| 4,941,221 | 7/1990 | Kanzler | 5/615 |
| 4,974,692 | 12/1990 | Carruth et al. | 5/600 |
| 4,977,629 | 12/1990 | Jones | 5/715 |
| 5,029,352 | 7/1991 | Hargest et al. | 5/689 |
| 5,103,519 | 4/1992 | Hasty | 5/715 |
| 5,154,185 | 10/1992 | Latimer et al. | 5/628 |
| 5,184,612 | 2/1993 | Augustine | 5/482 |
| 5,201,102 | 4/1993 | McClure | 5/715 |
| 5,300,101 | 4/1994 | Augustine et al. | 5/482 |
| 5,300,102 | 4/1994 | Augustine et al. | 5/482 |
| 5,324,320 | 6/1994 | Augustine et al. | 5/482 |
| 5,336,250 | 8/1994 | Augustine | 5/423 |
| 5,350,417 | 9/1994 | Augustine | 607/104 |
| 5,390,382 | 2/1995 | Hannant et al. | 5/424 |
| 5,390,383 | 2/1995 | Carn | 5/624 |
| 5,394,577 | 3/1995 | James et al. | 5/715 |
| 5,402,542 | 4/1995 | Viard | 5/421 |
| 5,444,878 | 8/1995 | Kang | 5/421 |
| 5,533,218 | 7/1996 | Fahy | 5/421 |
| 5,556,169 | 9/1996 | Parrish et al. | 5/713 |
| 5,606,785 | 3/1997 | Shelberg et al. | 5/715 |
| 5,630,238 | 5/1997 | Weismiller et al. | 5/600 |

FOREIGN PATENT DOCUMENTS

| | | |
|---|---|---|
| 0 292 218 | 11/1988 | European Pat. Off. . |
| 2 435 245 | 4/1980 | France . |
| 2 493 695 | 5/1982 | France . |
| 2 648 706 | 12/1990 | France . |
| 937 724 | 1/1956 | Germany . |
| 2 200 823 | 7/1973 | Germany . |
| 82 28 688 | 1/1983 | Germany . |
| 44 47 431 | 6/1996 | Germany . |
| 678 390 | 9/1991 | Switzerland . |
| WO 87/06209 | 10/1987 | WIPO . |
| WO 97/12531 | 4/1997 | WIPO . |

*Primary Examiner*—Alexander Grosz
*Attorney, Agent, or Firm*—Barnes & Thornburg

[57] ABSTRACT

A surface pad system for a surgical table includes a cover having an upwardly-facing patient-support surface defining an interior region of the surface pad system, and a vacuum bead bag received in the interior region. The vacuum bead bag includes a flexible cover defining an interior region containing compressible beads including a lower layer of compressible beads and an upper layer of compressible bead separated from the lower layer of compressible beads by a membrane made from a flexible material. The system also includes a bladder received in the interior region of the cover and positioned to lie beneath the vacuum bead bag. The bladder defines an interior region and is inflatable when pressurized fluid is received in the interior region of the bladder so that the vacuum bead bag conformingly engages the patient on the patient-support surface when the bladder is inflated.

28 Claims, 8 Drawing Sheets

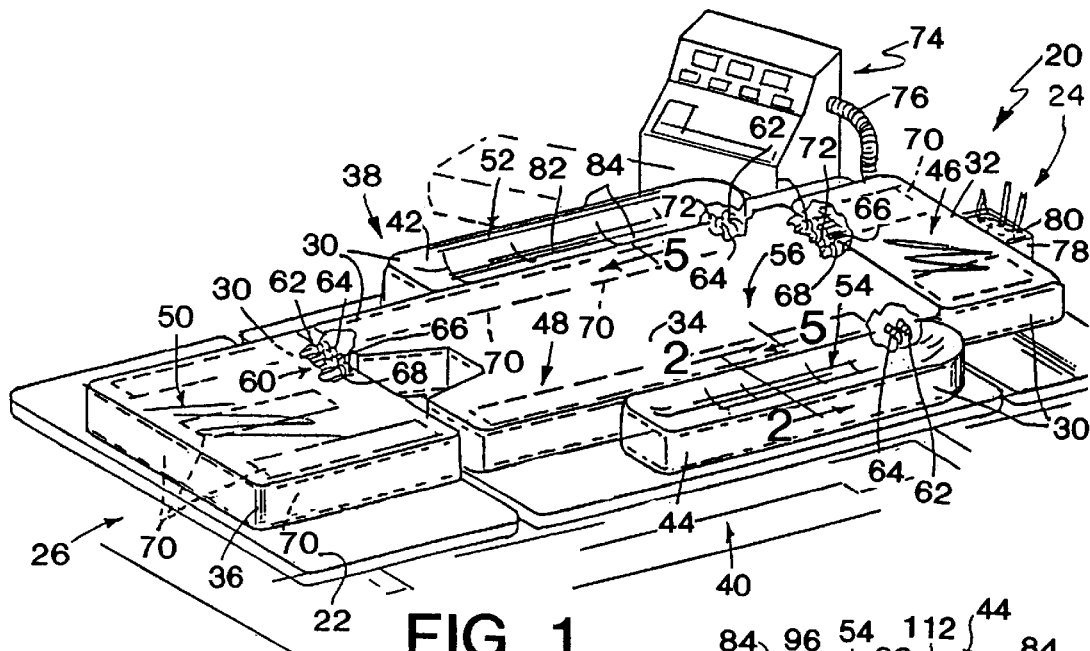

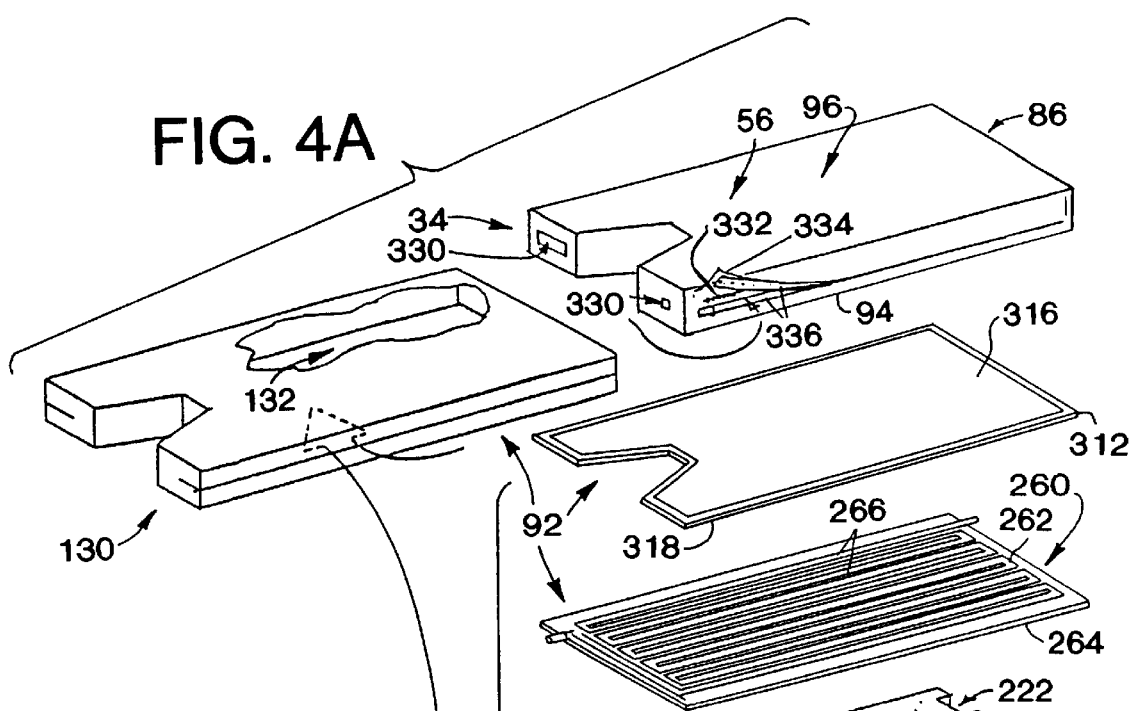
FIG. 4A
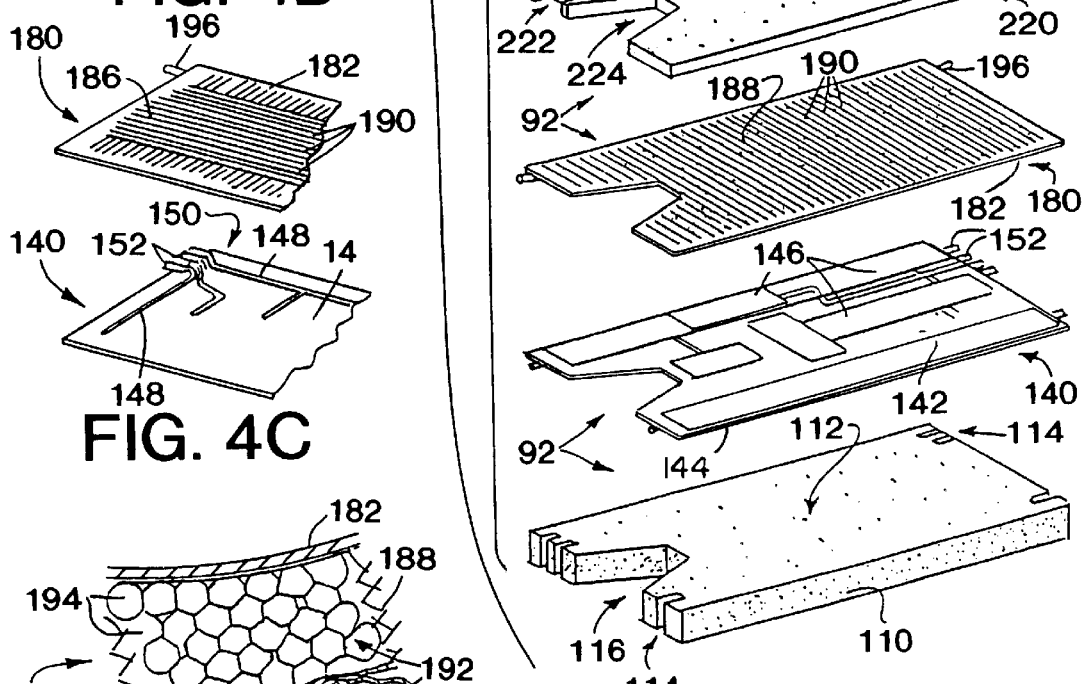
FIG. 4B
FIG. 4C
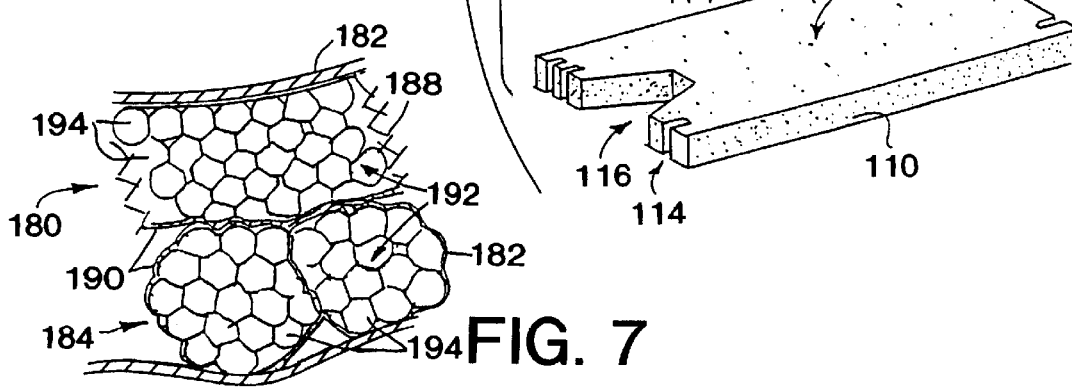
FIG. 7

SURFACE PAD SYSTEM FOR A SURGICAL TABLE

BACKGROUND SUMMARY OF THE INVENTION

The present invention relates to a surgical table for use in a hospital operating room, and particularly to a surface pad system for a surgical table, the surface pad system being carried by a generally horizontal upwardly-facing table-top surface of the surgical table and being positioned to lie beneath the patient. More particularly, the present invention relates to a surface pad system that can regulate the temperature of the patient, assist in positioning the patient, and that minimizes the interface pressure between the patient and a patient-support surface of the surface pad system thereby minimizing the occurrence of pressure ulcers and neuropathy caused by prolonged exposure of the patient to high interface pressures between the patient and the patient-support surface.

It is known to provide surface covers for operating tables for supporting patients above a table-top surface of the surgical table. Conventional surface covers typically include a foam rubber core surrounded by ticking material. It is also known to provide a gel pad between the foam rubber and a top panel of the ticking material covering the foam rubber. In addition, these operating table surface covers are typically provided in the form of a set of pads including a head pad supporting the head of the patient, a body pad supporting the torso of the patient, and a foot pad supporting the lower legs and feet of the patient. Occasionally, these sets include a fourth pad positioned longitudinally between the body pad and the foot pad and supporting the sacrum of the patient.

It is also known to provide a patient support having an upwardly-facing top surface, the temperature of which is controlled. For example, U.S. Pat. No. 5,402,542 to Viard, which is assigned to the assignee of the present invention, discloses a fluidized patient support having a temperature-controlled top surface supporting the patient.

It is also known to provide inflatable bladders and inflatable cushions in mattresses which can be inflated and deflated to assist a caregiver when turning a patient relative to the sleeping surface of the mattress. For example, U.S. Pat. No. 5,269,0302 Pahno et al. discloses an apparatus and method for managing waste for patient care, the apparatus including inflatable sacks which assist turning the patient to facilitate cleansing of the patient. In addition, U.S. Pat. Nos. 4,949,414 and 5,062,167 to Thomas et al., which are assigned to the assignee of the present invention, disclose a bi-modal turning method that utilizes a mattress including a plurality of identical multi-chambered inflatable sacks.

What is needed is a surface pad system for a surgical table that can assist with the regulation of the temperature of the patient on the patient-support surface, that can position the patient, and that minimizes the interface pressure at high pressure points between the patient and the patient-support surface. The patient-support surface of the surface pad system should be conformable to fit the contours of the patient and maximize the surface area of contact between the patient-support surface and the patient, thereby minimizing the interface pressure between the patient and the patient-support surface.

The surface pad system should also be capable of moving or rolling the patient from an initial position to a new position without requiring the members of the surgical team to reposition the anesthetized patient and without requiring the members of the surgical team to stuff pillows, towels, wedges, or other objects between the patient and the patient-support surface while manually holding the patient in the new position to keep the patient in the new position after the members of the surgical team stop holding the patient. In addition, once the patient is moved to the new position, the surface pad system should rigidly support the patient in the desired position. Finally, the patient-support system should maintain the patient at a comfortable temperature while the patient is awake, and once anesthetized, the patient-support system should assist in reducing the temperature of the patient to the desired operating temperature selected by the surgical team.

According to the present invention, a surface pad system is provided for a surgical table. The surface pad system includes a cover having an upwardly-facing patient-support surface, the cover defining an interior region of the surface pad system. A vacuum bead bag is received in the interior region of the surface pad system. The vacuum bead bag includes a flexible cover defining an interior region containing compressible beads. A bladder is received in the interior region of the cover and is positioned to lie beneath the vacuum bead bag. The bladder defines an interior region of the bladder and is inflatable when pressurized fluid is received in the interior region so that the vacuum bead bag conformingly engages the patient on the patient-support surface when the bladder is inflated.

In preferred embodiments the surface pad system includes a plurality of pad sections that are positioned to lie on the upwardly-facing table-top of a surgical table between the patient and the surgical table. The preferred surface pad system includes a head pad section positioned to lie beneath the head of the patient, a leg pad section longitudinally spaced apart from the head pad section and positioned to lie beneath the lower legs and feet of the patient, a body pad section positioned to lie between the head pad section and the leg pad section, and first and second arm pad sections each of which is positioned to lie beside the body pad section and beneath an arm of the patient.

Each pad section of the surface pad system includes a pad core received by a cover of the pad section. Each pad core includes a plurality of pad core elements. Preferably, each pad core includes a base foam support layer made from high density foam that is positioned to lie beneath the other pad core elements and that provides a structural foundation for the pad core.

Each preferred pad core also includes a bladder pad having one or more bladders in fluid communication with a pressurized fluid source and inflatable to a first pressure for pressing the patient-support surface against the patient to conform to the shape of the patient when the bladders are inflated to the first pressure. In addition, selected bladders can be inflated to a second pressure which is greater than the first pressure. Each selected bladder can be arranged relative to the pad section so that when the bladder is inflated to the second pressure, the bladder and the patient-support surface reposition the patient from an initial position to a new position by raising the portion of the patient-support surface above the bladder from its initial position to a higher position and repositioning the patient, for example, by causing the patient to tilt or roll away from the bladder. If desired, the bladder can be subsequently deflated to reduce the pressure in the bladder to the first pressure and causing the patient to move back to the initial position.

Also, each preferred pad section includes a vacuum bead bag which is preferably positioned to lie on top of the bladder pad. The vacuum bead bag includes a casing forming an interior region containing a plurality of tubes, each of which is filled with compressible beads. The interior region of the vacuum bead bag is in fluid communication with a vacuum source. When air is evacuated from the interior region of the vacuum bead bag, the compressible beads are compressed against one another and deform so that the beads are held immobile with respect to one another and the vacuum bead bag rigidly assumes the shape that it is in when the interior region is evacuated.

The vacuum bead bag in accordance with the present invention includes an upper layer of elongated tubes containing compressible beads and a lower layer of elongated tubes containing compressible beads. Each tube in the lower layer of the vacuum bead bag extends in a first direction. Each tube in the upper layer of the vacuum bead bag extends in a second direction. The second direction is different from the first direction, and preferably the second direction is generally perpendicular to the first direction. This "plywood" arrangement provides an extremely rigid support when the interior region of the vacuum bead bag is evacuated. By layering the tubes in the criss-crossing plywood arrangement with "grains" of each layer running in generally perpendicular direction provides support for the patient both in a longitudinal direction and in a lateral direction.

Each pad section of the surface pad system also preferably includes a pressure-reduction foam layer made from foam rubber which is positioned to lie on top of the vacuum bead bag. The pressure-reduction foam layer is made from a thermally active "visco-elastic" foam rubber material. When the foam layer is at a warmer temperature the foam is softer and more pliable and when the foam layer is at a cooler temperature the foam is harder and retains its shape.

When a patient is awake and the patient-support surface in maintained at a comfortable warm temperature, the visco-elastic pressure-reduction foam layer will tend to conform to the shape of the patient. After the patient is anesthetized and the temperature of the patient-support surface is lowered, the visco-elastic pressure-reduction foam layer will tend to retain its shape. Thus, if the position of the patient is changed during the course of a surgical procedure, once the patient is moved back into his or her original position, the pressure-reduction foam layer will have generally retained its original shape and thus will be shaped to receive the patient.

Each pad section of the surface pad system also includes a thermal pad which is preferably positioned to lie above the pressure-reduction foam layer. The thermal pad is positioned to lie above the pressure-reduction foam layer to maximize the effectiveness of the heat transfer between the thermal pad and the patient-support surface and to minimize the impact of the thermally insulating pressure-reduction foam layer on the heat transfer between the thermal pad and the patient-support surface.

The thermal pad includes a serpentine-shaped channel defined therein. A thermoregulation fluid is received in the channel and is circulated through the channel to maintain the temperature of the thermal pad and thus maintain the temperature of the patient-support surface near the temperature of the thermoregulation fluid. The channel is in fluid communication with a heat exchanger so that the temperature of the thermoregulation fluid, and thus the temperature of the patient-support surface, can be adjusted according to the desires of the surgical team by using the heat exchanger to adjust the temperature of the thermoregulation fluid flowing through the channel.

A gel pack is positioned to lie on top of the thermal pad. The gel pack includes a casing containing a viscous material such as a silicon polymer of the type used to produce prosthetic devices. The viscous material will tend to flow away from high interface pressure points and will tend to flow toward low interface pressure points, thus more evenly distributing the weight of the patient and buoying the patient away from the high interface pressure points, thereby minimizing the interface pressure between the patient and the patient-support surface at the high interface pressure points. Preferably, a thermocouple is positioned within the gel in the gel pack to provide feedback to the heat exchanger controlling the temperature of the thermoregulation fluid.

A cut-proof material is positioned to lie above the gel layer. The cut-proof material operates to protect the pad core, and particularly the gel layer, the thermal pad, and the bladder from puncture due to dropped scalpels, dropped needles, or other sharp objects. In addition, the cut-proof material is preferably placed along the sides of each pad section to provide additional protection against punctures and cuts.

The cover is formed to include an interior region surrounding the pad core and holding the pad core elements in place relative to one another. Preferably, the cover is made from a bi-directional stretch material that can be stretched both in a longitudinal direction and in a lateral direction. Use of a bi-directional stretch material eliminates folding of the cover material on itself during movement of portions of each pad section relative to other portions of each pad section. In addition, the cover is preferably made from a liquid impermeable material to both protect the pad core elements from exposure to fluids from outside of the cover and to protect the patient from exposure to fluids from the pad core elements in the event of rupture of the gel pack, the thermal pad, or one of the bladders. If desired, a fire proof sock can be positioned to lie between the pad core elements and the cover to assist with extinguishing flames after the pad core elements are exposed to flames, a characteristic required by regulations imposed by several regulating authorities.

The pad sections can be configured so that each pad section couples to each other pad section. For example, the head pad section can be coupled to the body pad section and the body pad section can be coupled to the leg pad section and both of the arm pad sections. Preferably, the channels formed in the thermal pads of each pad section are in fluid communication with one another so that the thermoregulation fluid circulates through the thermal pads of each pad section. Circulating the thermoregulation fluid through the thermal pad of each pad section allows for the temperature of the thermoregulation fluid to be regulated by a single heat exchanger rather than including a separate heat exchanger for the thermal pad of each pad section.

Likewise, the vacuum bead bag of each pad section can be in fluid communication with the vacuum bead bag of each other pad section. This coupling permits the use of only one vacuum source which is used to operate the vacuum bead bags of each pad section. Also, although the bladders in each of the pad sections are not in fluid communication with one another, the bladder pad in each pad section is formed to include an internally contained channel system eliminating the need to include hoses connected to each bladder. The channel system allows for the use of a single pressurized fluid source which can inflate and deflate the bladders of each pad section.

A controller is provided for the surface pad system in accordance with the present invention. The controller is used to control the operation of the heat exchanger, the vacuum source, and the pressurized fluid source. The use of a single controller to control each of the heat exchanger, the vacuum source, and the pressurized fluid source allows for the coordination of each of these systems. For example, the controller can be programmed to lower the temperature of the patient-support surface during surgical procedures at a predetermined cooling rate. However, if desired, the lowering of the temperature can be programmed to occur only after the bladders are inflated and after air is evacuated from the vacuum bead bags. In addition, a "chest-expanding" bladder can be provided in the body pad section which can be pressurized to hyperextend the chest cavity of a patient during surgical procedures. If desired, the controller can be programmed to allow this inflation of the chest-expanding bladder only after the temperature of the patient-support surface has been lowered to the desired operating temperature by the thermoregulation fluid in the thermal pad.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which:

FIG. 1 is a perspective view of a surface pad system in accordance with the present invention with portions broken away showing a plurality of pad sections and a control unit positioned to lie adjacent to the head end of the surface pad system, the control unit providing pressurized fluid, vacuum, and a temperature-controlled thermoregulation fluid to the pad sections, a head pad section adjacent to a head end of the surface pad system, a leg pad section longitudinally spaced-apart from the head pad section and positioned to lie near a foot end of the surface pad system, a body pad section positioned to lie between the head pad section and the leg pad section, the body pad section having first and second spaced-apart elongated sides, first and second arm pad sections positioned to lie adjacent to the first and second sides of the body pad section, respectively, conduits connecting the head, body, leg, and arm pad sections for flowing thermoregulation fluid therebetween, and additional conduits connecting the head, body, and leg pad sections to one another for flowing pressurized fluid and vacuum therebetween;

FIG. 2 is a sectional view taken along line 2—2 of FIG. 1 owing a concave top surface of the arm pad section, the arm pad section including a base foam portion made from high density foam, a thermal pad formed to include a channel through which thermoregulation fluid flows, the thermal pad being positioned to lie on top of the base foam layer, and a gel pack positioned on top of the thermal pad, the gel pack including a casing containing viscous fluid which flows within the casing to minimize the interface pressure between the patient and the top surface of the arm section;

FIG. 3 is a side view with portions broken away of the body pad section showing a cover defining an interior region of the body pad section, the interior region receiving a base foam support layer made from high density foam, a bladder pad positioned to lie on top of the base foam layer, a vacuum bead pad positioned to lie on top of the bladder pad and including a plurality of tubes containing compressible beads, the plurality of tubes defining an upper layer of tubes extending in a longitudinal first direction and a lower layer of tubes extending in a transverse second direction which is generally perpendicular to the first direction, an upper foam layer positioned to lie on top of the vacuum bead bag, a thermal pad positioned to lie on top of the upper foam layer, and a gel pack sandwiched between the thermal pad and the cover;

FIG. 4a is an exploded perspective view of the body pad section of the surface pad system of FIG. 1 showing a cover made from ticking material and defining an interior region of the cover receiving a pad core including the base foam support layer positioned beneath the bladder pad, and the vacuum bead bag, the upper foam layer, the thermal pad, and the gel pack, all of which are positioned above the bladder pad;

FIG. 4b is a view of the underside of the vacuum bead bag of FIG. 4a showing that longitudinally-extending tubes of compressible beads are positioned to lie beneath the transversely-extending tubes of compressible beads to produce a "plywood" effect;

FIG. 4c is a view of the underside of the bladder pad of FIG. 4a showing that the bladder pad is an integral pad formed to include channels on the underside of the bladder pad beneath the bladders on the upper side of the bladder pad;

FIG. 7 is an enlarged view of a portion of FIG. 6 showing the vacuum bead bag after air has been evacuated from the interior region of the vacuum bead bag so that the compressible beads have deformed against one another to become immobile relative to one another so that the vacuum bead bag is rigid and retains the shape that it attained prior to having the air evacuated from the interior region of the vacuum bead bag;

DETAILED DESCRIPTION OF THE DRAWINGS

Figure 5:
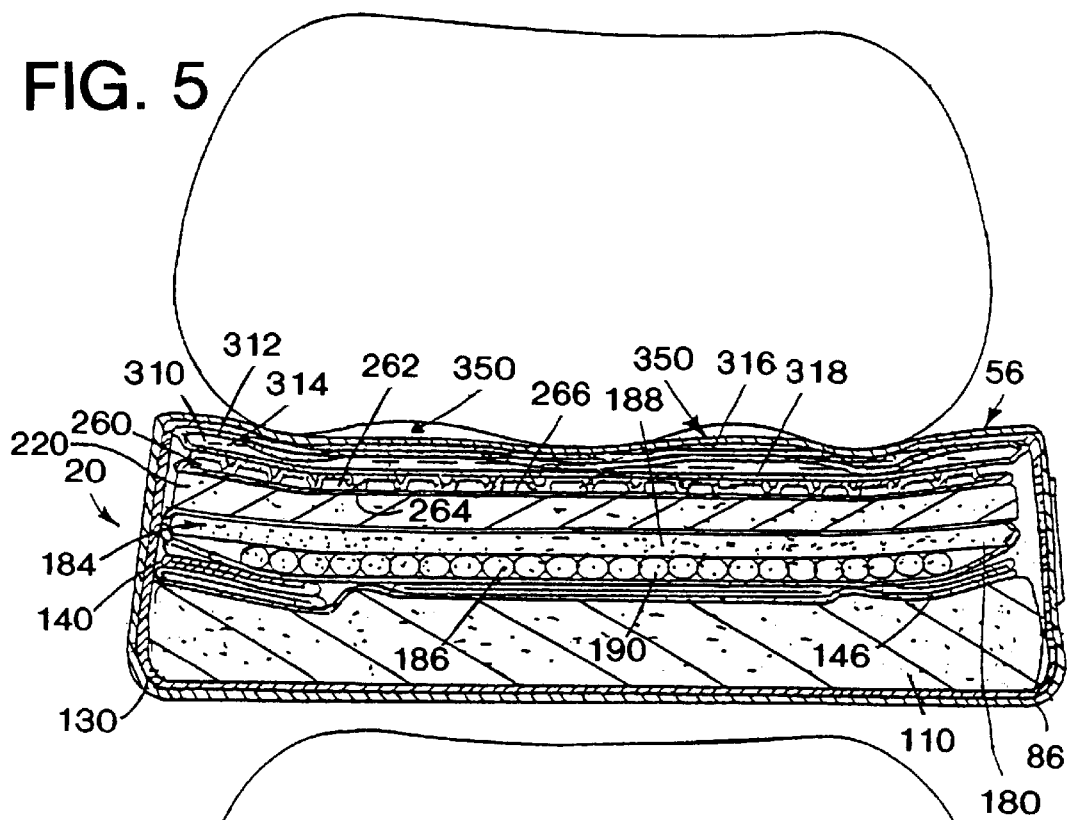
FIG. 5 is a sectional view taken along line 5—5 of FIG. 1 showing the body pad section of the surface pad system, a person lying on a patient-support surface of the surface pad system, and gaps formed between the patient-support surface and the patient.

A surface pad system 20 in accordance with the present invention includes a plurality of pad sections 30 carried by an upwardly-facing table-top 22 of a surgical table as shown in FIG. 1. Table-top 22 includes a head end 24, a foot end 26, a first side 38, and a second side 40. As used in this description, the phrase "head end 24" will be used to denote the end of any referred-to object that is positioned to lie nearest the head end 24 of table-top 22 and the phrase "foot end 26" will be used to denote the end of any referred-to object that is positioned to lie nearest foot end 26 of table-top 22. Likewise, the phrase "first side 38" will be used to denote the side of any referred-to object that is positioned to lie nearest first side 38 of table-top 22 and the phrase "second side 40" will be used to denote the side of any referred-to object that is positioned to lie nearest second side 40 of the table-top 22.

Surface pad system 20 includes a head pad section 32 positioned to lie on head end 24 of table-top 22, a leg pad section 36 longitudinally spaced apart from head pad section 32 and positioned to lie on foot end 26 of table-top 22, and a body pad section 34 positioned to lie therebetween as shown in FIG. 1. Surface pad system 20 further includes a first arm pad section 42 positioned to lie adjacent to first side 38 of body pad section 34 and a second arm pad section 44 positioned to lie adjacent to second side 40 of body pad section 34.

Head pad section 32 is formed to include an upwardly-facing top surface 46, body pad section 34 is formed to include an upwardly-facing top surface 48, leg pad section 36 is formed to include an upwardly-facing top surface 50, first arm pad section 42 is formed to include an upwardly-facing top surface 52, and second arm pad section 44 is formed to include an upwardly-facing top surface 54. Top surfaces 46, 48, 50, 52, 54 are spaced apart from table-top 22 of the surgical table by generally equivalent distances and are generally coplanar so that top surfaces 46, 48, 50, 52, 54 cooperate to define a generally horizontal upwardly-facing patient-support surface 56 of surface pad system 20.

Figure 14:
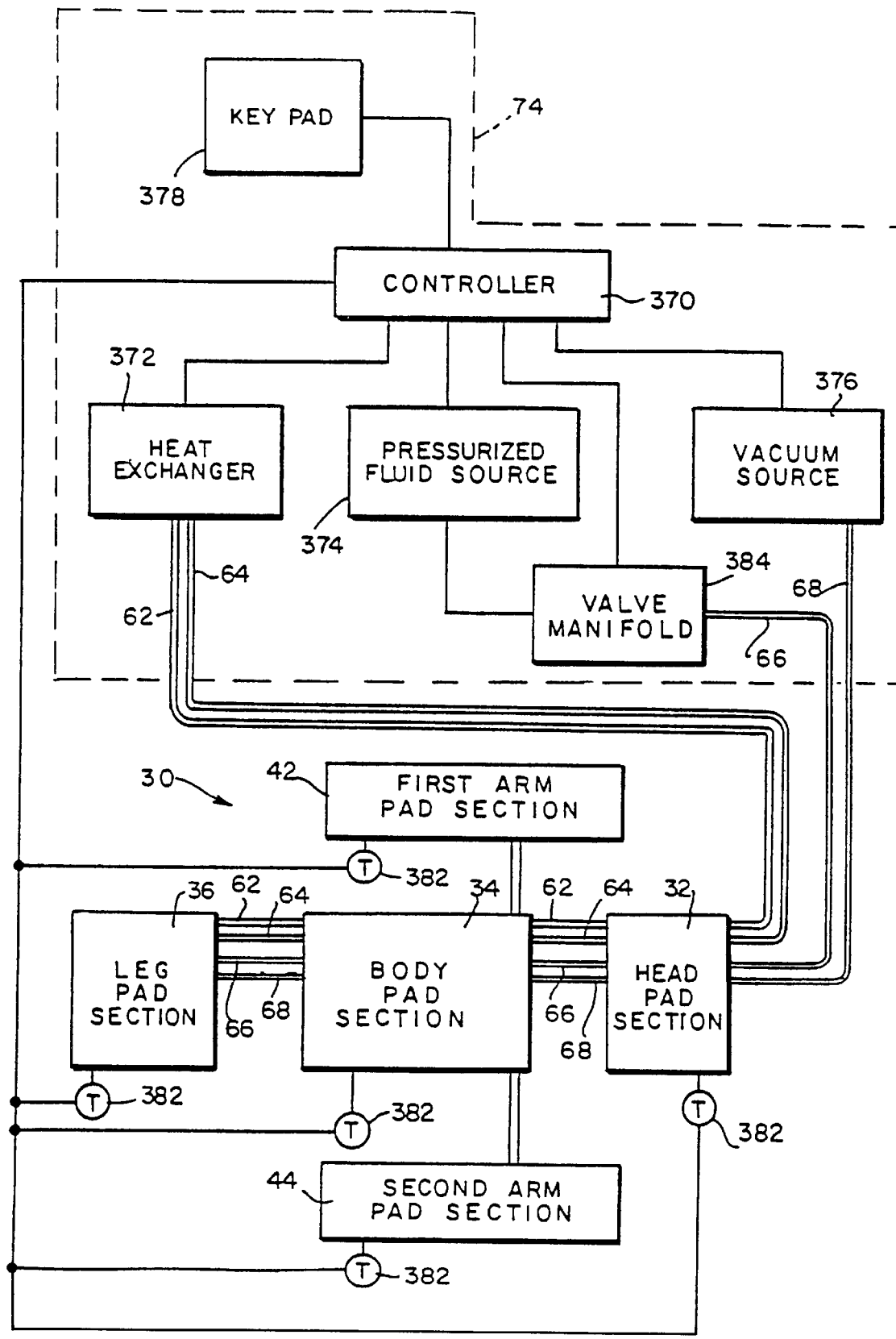
FIG. 14 is a diagrammatic view of a control system of the surface pad system showing the pad sections coupled to the control system including a heat exchanger, a pressurized fluid source, a vacuum source, a keypad, thermocouples, and a controller for communicating with and controlling the operation of the other elements of the control system.

Pad sections 30 are connected to one another by conduits 60 including a thermoregulation fluid supply conduit 62, a thermoregulation fluid return conduit 64, a pressurized fluid conduit 66, and a vacuum conduit 68 as shown in FIG. 1 and as shown diagrammatically in FIG. 14. Thermoregulation fluid supply conduit 62 brings surface pad system 20 into fluid communication with a heat exchanger 372 contained in a control housing 74 of surface pad system 20. Thermoregulation fluid return conduit 64 also brings surface pad system 20 into fluid communication with the source of thermoregulation fluid and return conduit 64 cooperates with supply conduit 62 to circulate thermoregulation fluid through surface pad system 20.

Pressurized fluid conduit 66 brings surface pad system 20 into fluid communication with a source of pressurized fluid 374. The pressurized fluid is preferably pressurized air, although the pressurized fluid can include pressurized water, pressurized treated water which is treated, for example, to have a viscosity greater than the viscosity of untreated water, or any other generally inert gaseous or liquid fluid that can be used as described below to operate surface pad system 20 without the scope of the invention as presently perceived.

Vacuum conduit 68 brings pad sections 30 of surface pad system 20 into fluid communication with a vacuum source 376. Vacuum source 376 can be manipulated to evacuate air from desired portions of pad sections 30 as described below and to allow air or any other selected gas that is generally inert to return to the evacuated portions of pad sections 30.

Each pad section 30 can be provided with cut-proof material 70 as shown in FIG. 1 to protect pad section 30 from puncture or penetration by dropped scalpels, dropped needles, or other sharp objects that inadvertently contact pad sections 30. Preferably, cut-proof material 70 is placed beneath patient-support surface 56 adjacent to sides 38, 40 of pad sections 30 and along other portions of patient-support surface 56 that are unlikely to be engaged by a patient resting on patient-support surface 56 but that might be susceptible to such damaging contact. In addition, cut-proof material 70 can be placed along generally vertically-extending side walls of pad sections 30 for additional protection.

Surface pad system 20 also includes control housing 74 as shown in FIG. 1, containing a controller 370 for controlling heat exchanger 372, source of pressurized fluid 374, and vacuum source 376, shown diagrammatically in FIG. 14. A key pad 378 is also carried by control housing 74 and is coupled to controller 370. Preferably, the thermoregulation fluid supply and return conduits 62, 64, the pressurized fluid conduit 66, and the vacuum conduit 68 all extend from control housing 74 to pad sections 30 through a single hose 76 as shown in FIG. 1. Preferably, hose 76 connects to surface pad system 20 near head end 24 of surface pad system 20 and adjacent to a needle receptacle 78.

Needle receptacle 78 contains a medium 80 such as foam rubber, steel wool, or some other porous material that can receive needles. Needle receptacle 78 provides a convenient storage location for anesthetists and other surgical team members to store needles so that the surgical team members can store needles in needle receptacle 78 instead of using pad sections 30 to store needles which presents the risk of puncturing pad sections 30.

Arm pad sections 42, 44 are pivotably coupled to body pad section 34 as shown in FIG. 1 so that arm pad sections 42, 44 can be pivoted away from sides 38, 40 of body pad section 34. Pivoting arm pad sections 42, 44 away from sides 38, 40 of body pad section 34 provides members of the surgical team with greater access to the patient carried on patient-support surface 56.

In addition, top surfaces 52, 54 of first and second arm pad sections 42, 44 each have a concave shape providing an elongated trough 82 which cooperates with a pair of elongated outer ridges 84 to cradle the arms of the patient carried on patient-support surface 56. Thus, first and second arm pad sections 42, 44 lift the arms of the patient to a position spaced apart above table-top 22 of the surgical table the same distance that top surfaces 46, 48, 50 of head, body and leg pad sections 32, 34, 36 are spaced apart from table-top 22, unlike some conventional coverings for surgical tables which allow the arms of the patient to dangle beside the covering. In addition, ridges 84 cooperate with trough 82 of top surfaces 52, 54 of arm pad sections 42, 44 to retain the arms of the patient on first and second arm pad sections 42, 44, respectively.

Each pad section 30 includes a cover 86 defining an interior region 88 receiving a pad core 90 which includes a plurality of pad core elements 92 as shown best in FIGS. 2–4a. For example, pad core 90 of illustrative second arm pad section 44 includes a high density foam base support layer 110, a thermal pad 260 engaging a top surface 112 of support layer 110, a gel pack 310 positioned to lie on top of thermal pad 260, and a fire sock 130 surrounding support layer 110, thermal pad 260, and gel pack 310 within interior region 88. Top surface 112 of support layer 110 has a concave shape and is bowed downwardly so that top surface 54 of second arm pad section 44 has the concave shape to cradle the arm of the patient on patient-support surface 56. Thermal pad 260, gel pack 310, fire sock 130, and cover 86 generally conform to the shape of top surface 112 of support layer 110 as shown in FIG. 2.

Although pad core 90 of illustrative second arm pad section 44 includes only the pad core elements 92 of high density base foam support layer 110, thermal pad 260, gel pack 310, and fire sock 130, other pad core elements 92 can be added to pad core 90 without exceeding the scope of the invention as presently perceived as shown, for example, in FIGS. 3 and 4a which show pad core elements 92 included in pad core 90 of illustrative body pad section 34.

Pad core 90 of body pad section 34 illustratively includes high density base foam support layer 110 received in an interior region 132 of fire sock 130 which is received in interior region 88 of cover 86. Support layer 110 engages fire sock 130 adjacent to a bottom 94 of cover 86 as shown in FIG. 3. A bladder pad 140 carrying bladders 146 for adjusting the support and firmness characteristics of body pad section 34 is received in interior region 88 and is positioned to lie on top of support layer 110. A vacuum bead bag 180 which can be manipulated between a pliable state and a rigid state retaining its shape is received in interior region 88 and is positioned to lie on top of bladder pad 140 and a pressure reduction foam layer 220 is received in interior region 88 and is positioned to lie on top of vacuum bead bag 180. Thermal pad 260 is received in interior region 88 and is positioned to lie on top of pressure reduction foam layer 220 and gel pack 310 is received in interior region 88 and is sandwiched between thermal pad 260 and a top 96 of cover 86. Surface pad system 20 can thus include pad sections 30 having pad core 90 including pad core elements 92 such as fire sock 130, support layer 110, bladder pad 140, vacuum bead bag 180, foam layer 220, thermal pad 260, and gel pack 310, or combinations thereof, without exceeding the scope of the invention as presently perceived.

When a patient is initially placed on patient-support surface 56, the room and patient-support surface 56 are typically warm to maximize the patient's comfort so that the patient can relax. Support layer 110, pressure reduction foam layer 220, and gel pack 310 can deform somewhat to meet the contours of the patient's body, particularly at the warmer temperature. A member of the surgical team can use key pad 378 to provide an instruction to controller 370 actuating bladder pad 140 and pushing patient-support surface 56 upwardly to even further conform to the contours of the patient's body and minimize high interface pressure points between the patient and patient-support surface 56. Another command can be provided to key pad 378 which causes vacuum bead bag 180 to change from a pliable state to a rigid state retaining the shape that vacuum bead bag 180 held when the command was provided. Once vacuum bead bag 180 is rigid, bladder pad 140 can be deactivated by providing a command through key pad 378, without having patient-support surface 56 lose its shape against the contours of the patient's body. Instead, rigid vacuum bead bag 180 will cause patient-support surface 56 to retain its shape against the contours of the patient's body.

If the surgical procedure to be performed on the patient requires the patient's temperature to be reduced, an instruction can be provided through key pad 378 that will cause the temperature of thermal pad 260 to decrease, withdrawing heat from patient-support surface 56 until patient-support surface 56 is at the desired temperature. If, during the course of the procedure, the patient is to be repositioned, rather than having members of the surgical team manually reposition the patient and stuff wedges, rolled-up towels, or other objects under the patient to keep patient at the new position, and then removing those objects afterward, an instruction can be provided through key pad 378 that will activate selected portions of bladder pad 140 to reposition the patient. Once the procedure is complete, the selected portions of bladder pad 140 can be deactivated to return the patient to the desired position.

Body pad section 34 includes cover 86 and pad core elements 92 as illustratively shown in FIG. 4a. Although FIG. 4a illustratively shows body pad section 34, the description below with respect to body pad section 34 applies generally to each pad section 30 and to pad core elements 92 of each pad section 30. As such, the description below with respect to body pad section 34 is to be taken as descriptive of each preferred pad section 30 and pad core elements 92 unless specifically stated otherwise.

Pad core elements 92 of body pad section 34 preferably include fire sock 130 received in interior region 88 of cover 86 and defining an interior region 132 surrounding the other pad core elements 92 as shown in FIG. 4a. Certain regulating authorities require articles such as surface pad system 20 to be self-extinguishing and including fire sock 130 improves the self-extinguishing characteristics of pad core elements 92. Preferred fire sock 130 is made from FIRE-GARD® SENTRYSAK™ material made by Spring Industries, Inc.

Pad core elements 92 of body pad section 34 also illustratively include high density base foam support layer 110 which is preferably positioned at the bottom of pad core 90 as illustratively shown in FIG. 4a. Support layer 110 is preferably a thermally active shock absorbing polyester visco-elastic foam such as model number SAF 50 50 foam produced by Fritz Nauer Limited of Switzerland. Support layer 110 forms a foundation of pad core 90 and body pad section 34 providing support for pad core elements 92 positioned to lie on top surface 112 of support layer 110.

If desired, top surface 112 of high density foam support layer 110 can be shaped as shown in FIG. 2 for second arm pad section 44, to contour top surface 48 of body pad section 34. As can be seen, each pad core element 92 that rests upon support layer 110 initially assumes the general shape of top surface 112 of support layer 110, as shown in FIGS. 2 and 3.

Preferred support layer 110 is formed from thermally active visco-elastic foam as mentioned above. Visco-elastic foam is formulated so that the firmness and support characteristics of the foam vary with the temperature of the foam, unlike conventional foam which maintains a generally constant durometer hardness and which provides the same support and firmness characteristics at each operating temperature. The preferred visco-elastic foam of support layer 110 is softer and more pliable at warmer temperatures and is firmer and tends to retain its shape at cooler temperatures. Thus, support layer 110 will easily conform to the shape of the patient carried on patient-support surface 56 at warmer temperatures, and if subsequently cooled, will tend to retain its shape even after the patient is removed from patient-support surface 56 or when the position of the patient on patient-support surface 56 is temporarily changed.

Support layer 110 is preferably sculptured from a unitary foam piece to shape support layer 110 for use in pad sections 30. Support layer 110 of body pad section 34 is illustratively shaped as shown in FIG. 4a and includes small cutouts 114 and a cavity 116. Cutouts 114 are configured to receive valves and couplings that couple pad sections 30 together so that these valves and couplings do not interfere with the support and firmness characteristics of patient-support surface 56. Cavity 116 provides the surgical team with access to the patient as needed for certain medical procedures. If desired, top surface 112 of support layer 110 can also be shaped without exceeding the scope of the invention as presently perceived, for example, to include a cavity such as an elongated and transversely-extending trough adjacent to the heels of the patient to reduce interface pressure between patient-support surface 56 and the heels of the patient.

Although preferred support layer 110 is sculptured from a unitary block of visco-elastic foam, it is within the scope of the invention as presently perceived to form support layer 110 from a plurality of foam blocks. For example, support layer 110 can include foam blocks having relatively plush support and firmness characteristics adjacent to the heel of the patient on patient-support surface 56 to minimize pressure ulcers on the heels of the patient.

Pad core elements 92 of body pad section 34 also illustratively include bladder pad 140 as shown in FIGS. 4a and 4c. Bladder pad 140 includes an upwardly-facing top sheet 142 and a downwardly-facing bottom sheet 144 engaging top surface 112 of high density foam layer 110. A plurality of bladders 146 are appended to top surface 142 and are strategically positioned to provide adjustable firmness and support characteristics for the patient on patient-support surface 56 when bladders 146 are inflated and deflated.

Bottom sheet 144 is appended to top sheet 142 of bladder pad 146 and cooperates therewith to define a plurality of channels 148 of a channel system 150 beneath top sheet 142 as shown best in FIG. 4c. Bladder pad 140 also includes a plurality of connectors 152 that are in fluid communication with the source of pressurized fluid 374. Connectors 152 are in fluid communication with channels 148 of channel system 150. Each bladder 146 is formed to include an interior region 156 and each channel 148 is in fluid communication with interior region 156 of at least one of bladders 146. Thus, channels 148 of channel system 150 are integrally appended to bladder pad 140 and eliminate the need to include a series of hoses or other fluid impermeable conduits for bringing connectors 152 into fluid communication with interior regions 156 of bladders 146.

Top sheet 142 of bladder pad 140 is formed to include an opening (not shown) extending therethrough. Bladder 146 is appended to top sheet 142 and is formed to include an opening (not shown) in fluid communication with the opening of top sheet 142 so that the opening of top sheet 142 is in fluid communication with interior region 156 of bladder 146. The opening of top sheet 142 is also in fluid communication with one of the channels 148 of channel system 150 so that pressurized fluid received in the channel is communicated to interior region 156 of bladder 146 through the opening in top sheet 142 and the opening in bladder 146 to inflate bladder 146. Likewise, pressurized fluid in interior region 156 of bladder 146 can be communicated to the channel through the opening of bladder 146 and the opening of top sheet 142 when bladder 146 is being deflated.

Including bladders 146 as a pad core element 92 of surface pad system 20 allows the surgical team to maximize the surface area of contact between the patient and patient-support surface 56, thereby minimizing the pressure of high interface pressure points between patient-support surface 56 and the patient, thus minimizing the possibility of forming pressure ulcers, neuropathy, or other disorders or conditions resulting from prolonged exposure to high interface pressure between patient and patient-support surface 56. In addition, including bladders 146 in pad sections 30 allows the surgical team to manipulate the position of the patient on patient-support surface 56 without undertaking the arduous task of manually repositioning the anesthetized patient and simultaneously stuffing a log of foam, a log of gel, a rolled-up towel, or another object underneath the anesthetized and manually positioned patient to hold the patient in the newly desired position. Instead, to manipulate the position of the patient on patient-support surface 56 of surface pad system 20 in accordance with the present invention, the surgical team needs to merely inflate or deflate a desired bladder 146, as described in more detailed hereinafter.

Illustrative and preferred bladder pad 140 is of unitary construction and is made from nylon mesh reinforced polyurethane. Illustrative bladder pad 140 is made from the 13 mil (0.33 mm) thick supported polyurethane film produced by Cooley Inc., of Pawtucket, R.I. Channel system 150 can be formed by R.F. welding bottom sheet 144 to top sheet 142. A free-flow connector 152 is preferably added to ends of each channel 148 to keep the channel open so that pressurized fluid can flow therethrough.

Pad core elements 92 of body pad section 34 also illustratively include vacuum bead bag 180 which is received in interior region 88 of cover 86 and is positioned to lie on top of bladder pad 140 as shown in FIGS. 4a and 4b. Vacuum bead bag 180 includes an outer casing 182 defining an interior region 184 in fluid communication with vacuum source 376 through fittings 196 and vacuum conduit 68. Thus, the atmosphere in interior region 184 of casing 182 can be evacuated by vacuum source 376 or can be replaced through fittings 196 and conduit 68.

Interior region 184 of vacuum bead bag 180 receives a lower layer 186 of compressible beads 194 and an upper layer 188 of compressible beads 194 as shown best in FIGS. 4a, 4b, and 7. Lower and upper layers 186, 188 each includes a plurality of elongated tubes 190 and each tube 190 is made from a flexible material defining an interior region 192 of tube 190 as shown best in FIG. 7.

Flexible tubes 190 are preferably made from a nylon mesh material having an opening size that is small enough to contain compressible beads 194 within interior regions 192 of tubes 190 while allowing the passage of the air or other gas comprising the atmosphere inside of interior region 184 of vacuum bead bag 180 therethrough. Although in preferred embodiments elongated tubes 190 are made from nylon mesh, any semipermeable material having an opening size small enough to contain compressible beads 194 therein while allowing the free passage therethrough of air or any other gas comprising the atmosphere of interior region 184 of vacuum bead bag 180 can be used without exceeding the scope of the invention as presently perceived.

In preferred embodiments, compressible beads 194 are white polystyrene beads made by Huntsman Chemical Corporation of Chesapeake, Va. and the beads preferably have a diameter between 1.5 and 2.5 mm (0.06–0.1 inches). Preferably, the polystyrene beads 194 are allowed to outgas (air out) prior to incorporation into surface pad system 20 in accordance with the present invention so that beads 194 are firmer than polystyrene beads that have not outgassed. Although preferred beads 194 are made from polystyrene, it is within the scope of the invention as presently perceived to provide beads 194 for vacuum bead bag 180 made from any compressible material that will allow beads 194 to deform as described below with reference to FIG. 7.

Lower layer 186 of vacuum bead bag 180 includes a plurality of longitudinally-extending tubes 190, each tube 190 being filled with compressible beads 194 as shown, for example, in FIG. 7 and each tube 190 extending in a direction generally parallel to the direction that each other tube 190 of lower layer 186 extends as shown in FIG. 4b. Upper layer 188 of vacuum bead bag 180 also includes a plurality of tubes 190. Tubes 190 of upper layer 188 extend in a transverse direction, each tube 190 being filled with compressible beads 194 and each tube 190 of upper layer 188 extending a direction generally parallel to the direction that each other tube 190 of upper layer 188 extends. Tubes 190 of upper layer 188 rest on top of tubes 190 of lower layer 186 as shown in FIGS. 4a, 4b, and 7.

Vacuum bead bag 180 thus includes lower layer 186 having a plurality of tubes extending in one direction and upper layer 188 having a plurality of tubes extending in a second direction. Preferably, the second direction is generally perpendicular to the first direction to provide vacuum bead bag 180 with a "plywood effect." The plywood effect of upper and lower layers 188, 186 provides increased strength and support to vacuum bead bag 180 when air is evacuated from interior region 184 and thus to patient-support surface 56 than would be provided by a conventional vacuum bead bag (not shown) having a single layer of beads.

Pad core elements 92 of body pad section 34 additionally include pressure reduction foam layer 220 which is received in interior region 88 of cover 86 and is positioned to lie above and engaging vacuum bead bag 180 as shown in FIG. 4a. Pressure reduction foam layer 220 provides pressure reduction to assist in reducing the pressure of high interface pressure points between the patient and patient-support surface 56.

Illustrative and preferred pressure reduction foam layer 220 is made from a thermally active shock absorbing polyester foam that is formulated as a visco-elastic foam, Model No. SAF 65180 foam produced by Fritz Nauer Limited of Switzerland. Thus, the support and firmness characteristics of pressure reduction foam layer 220 varies with the temperature of the foam in a manner similar to that described above with reference to support layer 110. Pressure reduction foam layer 220 is softer and more pliable at warmer temperatures and is firmer and tends to retain its shape at cooler temperatures. Thus, pressure reduction foam layer 220 will easily conform to the shape of the patient carried on patient-support surface 56 at warmer temperatures, and if subsequently cooled, will tend to retain its shape even after the patient is removed from patient-support surface 56 or when the position of the patient or patient-support surface is temporarily changed.

In preferred embodiments, pressure reduction foam layer 220 is sculptured from a unitary foam block to shape pressure reduction foam layer 220 for use in pad sections 30. Pressure reduction foam layer 220 of body pad section 34 is formed to include small cut-outs 222 for receiving portions of couplings, fittings, or valves so that the couplings, fittings, or valves do not interfere with the support and firmness characteristics of pad sections 30. In addition, pressure reduction foam layer 220 is sculptured to include a cavity 224 which is configured to provide access to the surgical team to desired portions of the patient on patient-support surface 56 during selected medical procedures. If desired, pressure reduction foam layer 220 can also be shaped to include a cavity such as, for example, an elongated and transversely-extending trough adjacent to the heels of the patient to reduce interface pressure between patient-support surface 56 and the heels of the patient without exceeding the scope of the invention as presently perceived.

Although preferred pressure reduction foam layer 220 is sculptured from a unitary block of visco-elastic foam, it is within the scope of invention as presently perceived to form pressure reduction foam layer 220 from a plurality of foam blocks. For example, pressure reduction foam layer 220 can include foam blocks having relatively plush support and firmness characteristics adjacent to the heel of the patient on patient-support surface 56 to minimize pressure ulcers on the heels of the patient.

Pad core elements 92 of body pad section 34 additionally include a thermal pad 260 received in interior region 88 of cover 86 and positioned to lie on top of pressure reduction foam layer 220 as shown in FIG. 4a. Thermal pad 260 includes a top sheet 262 that cooperates with a bottom sheet 264 to define a generally longitudinally-extending serpentine-shape channel 266 therebetween. Illustrative and preferred top and bottom sheets 262, 264 are made from nylon mesh reinforced urethane sheets such as the 13 mil (0.33 mm) thick supported polyurethane film produced by Cooley Inc., of Pawtucket, R.I. Top sheet 262 and bottom sheet 264 are R.F. welded to form channel 266 therebetween.

Thermoregulation fluid is received in channel 266 and is circulated between channel 266 of thermal pad 260 and heat exchanger 372 that is housed within control housing 74 for controlling the temperature of thermoregulation fluid in channel 266. Heat exchanger 372 controls the temperature of the thermoregulation fluid circulating through channel 266 so that thermal pad 260 can heat or cool patient-support surface 56 to a desired temperature selected by members of the surgical team.

As described above, thermal pad 260 is positioned to lie on top of pressure reduction foam layer 220 which is above vacuum bead bag 180 and bladder pad 140 as shown in FIG. 4a. Pressure reduction foam layer 220 is a thermal insulator that would impede the transfer of heat between thermal pad 260 and patient-support surface 56 if pressure reduction foam layer 220 were interposed between thermal pad 260 and patient-support surface 56 so that placing pressure reduction foam layer 220 beneath thermal pad 260 removes this impediment to heat transfer.

In addition, as described above, inflation of bladders 146 maximizes the surface area of contact between the patient and patient-support surface 56. Maximizing the surface area of contact also maximizes the conductive heat transfer between patient-support surface 56 and the patient. Placing thermal pad 260 above bladders 146 causes bladders 146 to press thermal pad 260 upwardly toward top 96 of cover 86 to maximize the conductive heat transfer from thermal pad 260 to top 96 of cover 86 and thus to patient-support surface 56.

Pad core elements 92 of pad core 90 of illustrative body pad section 34 also include gel pack 310 which is received in interior region 88 of cover 86 and which is positioned to lie on top of thermal pad 260 as shown in FIG. 4a. Gel pack 310 includes a casing 312 receiving a viscous fluid 314. Viscous fluid 314 flows away high interface pressure points and toward low interface pressure points to buoy the patient on patient-support surface 56 around high interface pressure points minimizing the interface pressure between the patient and patient-support surface 56 at the high interface pressure points.

Casing 312 of preferred gel pack 310 is made from a light weight urethane having a thickness of 6 mils (0.15 mm) such as polyurethane film Model No. EXR-625FS, natural film, made by J.B. Elastometrics Corporation of North Hampton, Mass. In addition, illustrative and preferred viscous fluid 314 is made from silicone-based polymer material such as that used for prosthetic devices including Oasis fabricated by TRU-LIFE of Dublin, Ireland.

As described above, pad core elements 92 are received in interior region 88 of cover 86 as shown in FIG. 4a. Preferred cover 86 is made from a bi-directional stretch ticking material that unlike conventional ticking materials can stretch in both a longitudinal direction and in a lateral direction. Use of the bi-directional stretch material allows cover 86 of body pad section 34 to move and bend without folding against itself. The preferred ticking material is a dual coated polyester including a net of dual coated urethane such as Via Tex 2 material, Manufacturing Quality No. T5793 made by Pen-Nyla of Nottingham, England.

Cover 86 is formed to include openings 330 allowing for the passage of conduits 60 therethrough and is formed to include an opening (not shown) for allowing the passage of pad core 90 into and out of interior region 88 of cover 86. A zipper 332 surrounds the opening for allowing the passage of pad core 90 and the zipper can be opened and closed to open and close the opening as shown in FIG. 4a. Cover 86 is additionally formed to include a flap 334 covering zipper 332. Flap 334 is appended to a portion of cover 86 above zipper 332 and flap 334 attaches to a side of cover 86 below zipper 332 by hook-and-loop type fasteners 336. In addition, illustrative and preferred cover 86 also includes hook-and-loop type fasteners (not shown) fixed to bottom 94 of cover 86 for attaching body pad section 34 to table-top 22 of the surgical table.

When a patient initially lies on body pad section 34, gel pack 310 will deform having viscous fluid 314 flow within casing 312 away from downwardly projecting portions of the patient that result in high interface pressure points between the patient and patient-support surface 56. This movement of viscous fluid 314 away from high interface pressure points and toward lower pressure interface points operates to increase the surface area of contact between the patient and patient-support surface as shown in FIG. 5. In addition, both pressure reduction foam layer 220 and high density foam layer 110 will deform in a like manner to minimize the interface pressure at high interface pressure points between the patient and patient-support surface 56. However, gaps 350 will typically still be found between the patient and the patient-support surface and relatively high interface pressure points will still exists between the patient and patient-support surface 56 as described below with reference to FIGS. 13a, 13b, and 13c.

As described above, support layer 110 and pressure reduction foam layer 220 are both made from a thermally active visco-elastic foam that is more pliable and more readily conforms to the shape of the patient at warmer temperatures than it does at cooler temperatures. The visco-elastic foam of support layer 110 and pressure reduction foam layer 220 cooperates with gel pack 310 to cause patient-support surface 56 to deform and move away from high interface pressure points between the patient and patient-support surface 56, thereby increasing the surface area of contact between the patient and patient-support surface 56 and reducing the interface pressure at high interface pressure points between the patient and patient-support surface 56, particularly when the patient first enters patient-support surface 56 and the temperature of patient-support surface 56 is warmer and enhancing the comfort of the patient.

Figure 6:
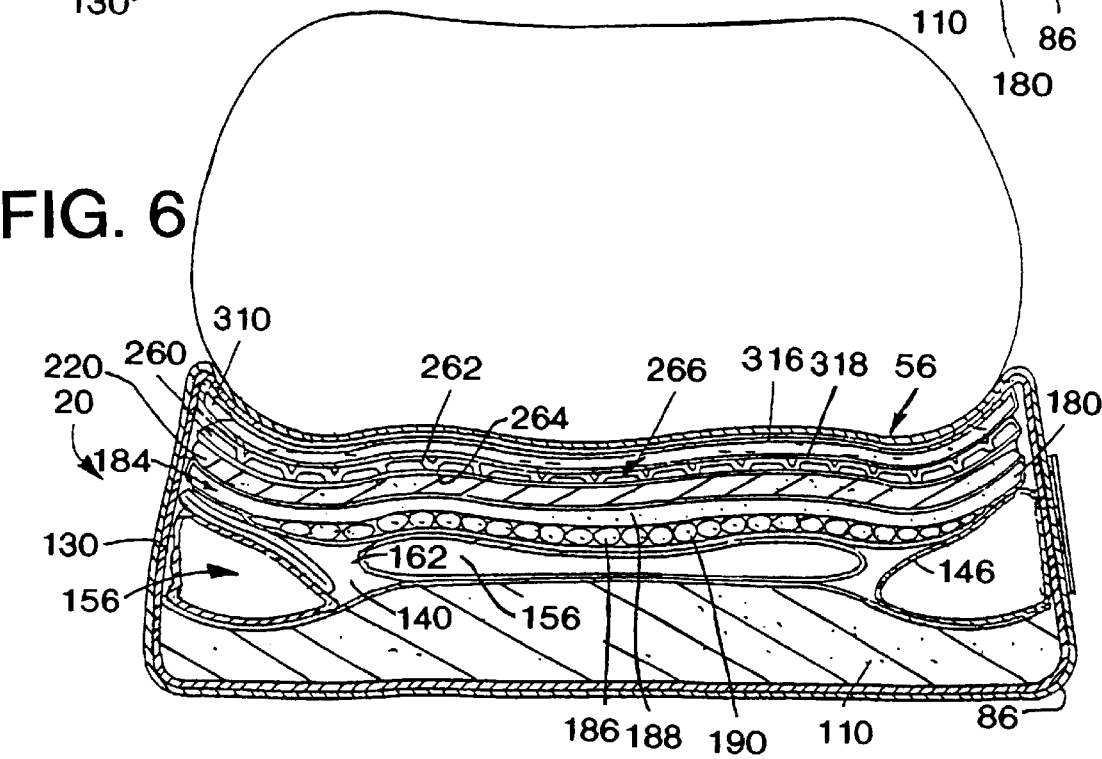
FIG. 6 is a view similar to FIG. 5 of the surface pad system after the bladders have been inflated and expanded showing the patient-support surface pressed against the patient by the bladders and conforming to the shape of the patient to maximize the surface area of contact between the patient and the patient-support surface and thereby more evenly distribute the weight of the patient across the patient-support surface.

Once the patient is resting on patient-support surface 56 and visco-elastic foam layers 110, 220 and gel pack 310 have reshaped in response to the weight of the patient, bladders 146 of bladder pad 140 can be inflated as shown in FIG. 6. The inflation of bladders 146 operates to press patient-support surface 56 upwardly against the patient and into gaps 350 formed between the patient and patient-support surface 56, thereby minimizing the gaps therebetween. Minimizing gaps 350 between the patient and patient-support surface 56 maximizes the surface area of contact between the patient and patient-support surface 56, thereby evenly distributing the weight of the patient across patient-support surface 56 and minimizing the interface pressure of the highest remaining interface pressure points between the patient and patient-support surface 56. Maximizing the surface area of contact between the patient and patient-support surface 56 also maximizes the conductive heat transfer between the patient and patient-support surface 56.

Inflating bladders 146 to press patient-support surface 56 against the patient and thereby more evenly distribute the weight of the patient across patient-support surface 56 also maximizes the efficacy of gel pack 310 as shown in FIG. 6. Before bladders 146 are inflated, as shown in FIG. 5, a top wall 316 of casing 312 is pressed against a bottom wall 318 of casing 312 at several locations indicating that additional relief of high interface pressure points is needed. Evenly distributing the weight of the patient across patient-support surface 56 by inflating bladders 146 also operates to more evenly distribute viscous fluid 314 across casing 312 of gel pack 310 to minimize the area of locations at which top wall 316 of casing 312 engages bottom wall 318 of casing 312. Minimizing the engagement between top wall 316 and bottom wall 318 maximizes the effectiveness of gel pack 310 and minimizes the interface pressure of the highest interface pressure points between the patient and patient-support surface 56.

Inflating bladders 140 also causes pad core elements 92 positioned between bladder pad 140 and patient-support surface 56, including vacuum bead bag 180, to conform to the shape of patient-support surface 56 as shown in FIG. 6. Once bladders 146 have been inflated, pushing patient-support surface 56 against the contours of the surface of the patient engaging patient-support surface 56 and filling gaps 350 that were initially formed between the patient and patient-support surface 56, the air can be evacuated from interior region 184 of casing 182 of vacuum bead bag 180.

Evacuating the air from vacuum bead bag 180 causes casing 182 to compress and causes compressible beads 194 to compress against one another as shown best in FIG. 7. Compression of beads 194 against one another eliminates the ability of beads 194 to move with respect to one another thus causing vacuum bead bag 180 to rigidly assume the shape held by vacuum bead bag 180 when the air was evacuated from interior region 184 of casing 182. Vacuum bead bag 180 will thus rigidly retain the shape conforming to the shape of patient-support surface 56 shown in FIG. 6 so long as the air remains evacuated from vacuum bead bag 180. In addition, by forming vacuum bead bag 180 to include lower layer 186 having a plurality of longitudinally-extending tubes 190 and upper layer 188 having a plurality of transversely extending elongated tubes 190 results in the plywood effect in which vacuum bead bag 180 provides a rigid support both in the longitudinal direction and in the transverse direction.

Figure 8:
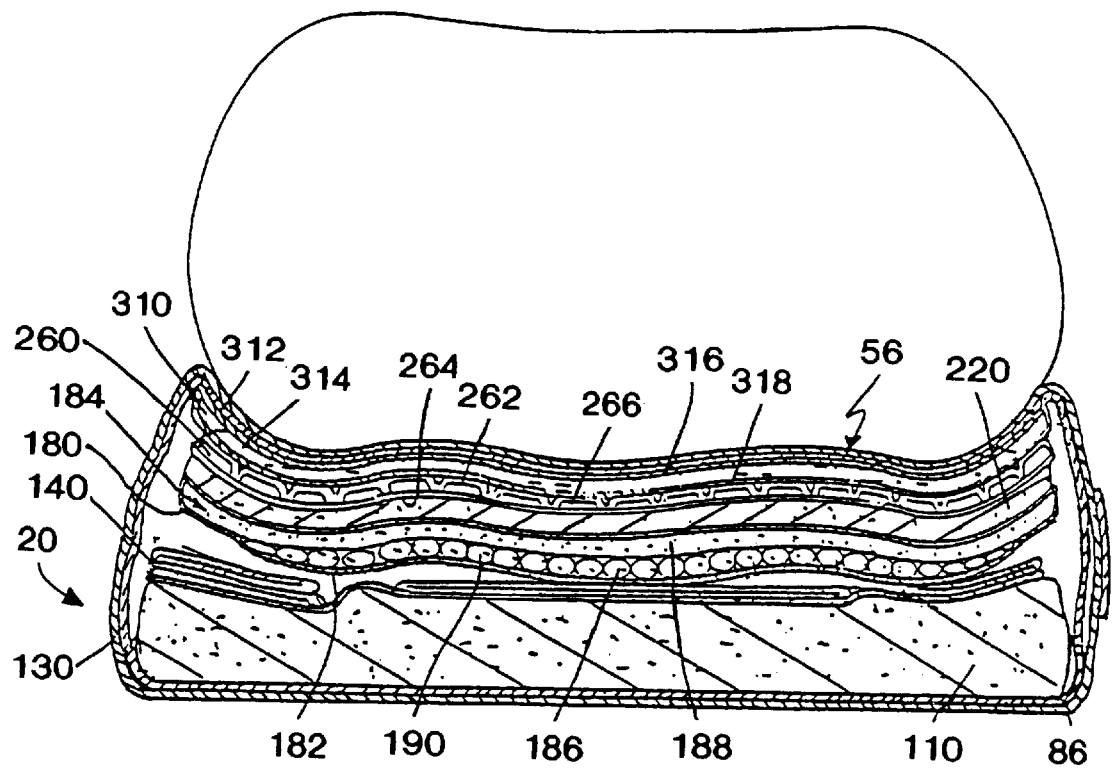
FIG. 8 is a view similar to FIG. 6 showing the surface pad system after the air has been evacuated from the interior region of the vacuum bead bag and after the bladders have been deflated so that the now rigid vacuum bead bag causes the patient-support surface to retain the shape conforming to the shape of the patient resting on top of the patient-support surface while allowing the bladders to be deflated to reduce the resiliency of the surface pad system so that the patient is firmly supported by the table to minimize the vibration and bouncing movement of the patient during surgical procedures.

Once air is evacuated from vacuum bead bag 180, bladders 146 can be deflated as shown in FIG. 8. Because vacuum bead bag 180 rigidly assumes the shape that it had immediately before air was evacuated from interior region 84, and because vacuum bead bag 180 is positioned to lie in interior region 88 of cover 86 on top of bladder pad 140 and bladders 146, deflating bladders 146 does not effect the conformal fit achieved between the patient and patient-support surface 56. However, by deflating bladders 146, the patient is more firmly and solidly supported than when the patient is resting on inflated bladders 146 which may act as resilient "balloons" allowing patient to vibrate or bounce.

Once the patient and surface pad system 20 are both properly positioned and configured as shown in FIG. 8, the patient can be anesthetized and, if desired, surface pad system 20 can be used to lower the temperature of patient-support surface 56. As described above, thermoregulation fluid circulates between channels 266 of thermal pads 260 and heat exchanger 372 which is carried in control housing 74. The temperature of the thermoregulation fluid and, thus, of thermal pad 260 and patient-support surface 56 is adjusted by adjusting the amount of heat added or removed from the thermoregulation fluid by heat exchanger 372. The control of heat exchanger 372 is described in more detail below with reference to FIG. 14.

Preferably, heat exchanger 372 is a so-called "Peltier device" for heating and cooling the thermal regulation fluid and contains no freon or other regulated chlorofluorocarbons (CFCs) or other ozone depleting chemicals. In preferred embodiments, the thermoregulation fluid is water which circulates between the Peltier device and the channels 266 of thermal pads 260, although any generally inert fluid having suitable heat capacity and viscosity characteristics can be used as the thermoregulation fluid without exceeding the scope of the invention as presently perceived.

Also in preferred embodiments, thermocouple 382 is received in gel pack 310 and is carried within casing 312 along with viscous fluid 314. The thermocouple measures the temperature of viscous fluid 314 of gel pack 310 and provides a temperature input signal in response thereto. The temperature input signal is received by a controller 370 which is carried in control housing 74 as shown diagrammatically in FIG. 14. Controller 370 receives the temperature input signal and provides a heat exchange output signal in response to the temperature input signal. Heat exchanger 372 receives the heat exchange output signal from the controller and adjusts the temperature of the thermoregulation fluid until the temperature input signal from the thermocouple indicates that the thermocouple has reached a desired temperature. It will be understood by those skilled in the art that although the temperature input signal indicates the temperature of viscous fluid 314 in gel pack 310, the proximity of gel pack 310 to patient-support surface 56 makes measurement of the temperature of gel pack 310 an adequate estimate of the temperature of patient-support surface 56 and the difference therebetween can be adequately compensated for by controller 370.

Figure 9:
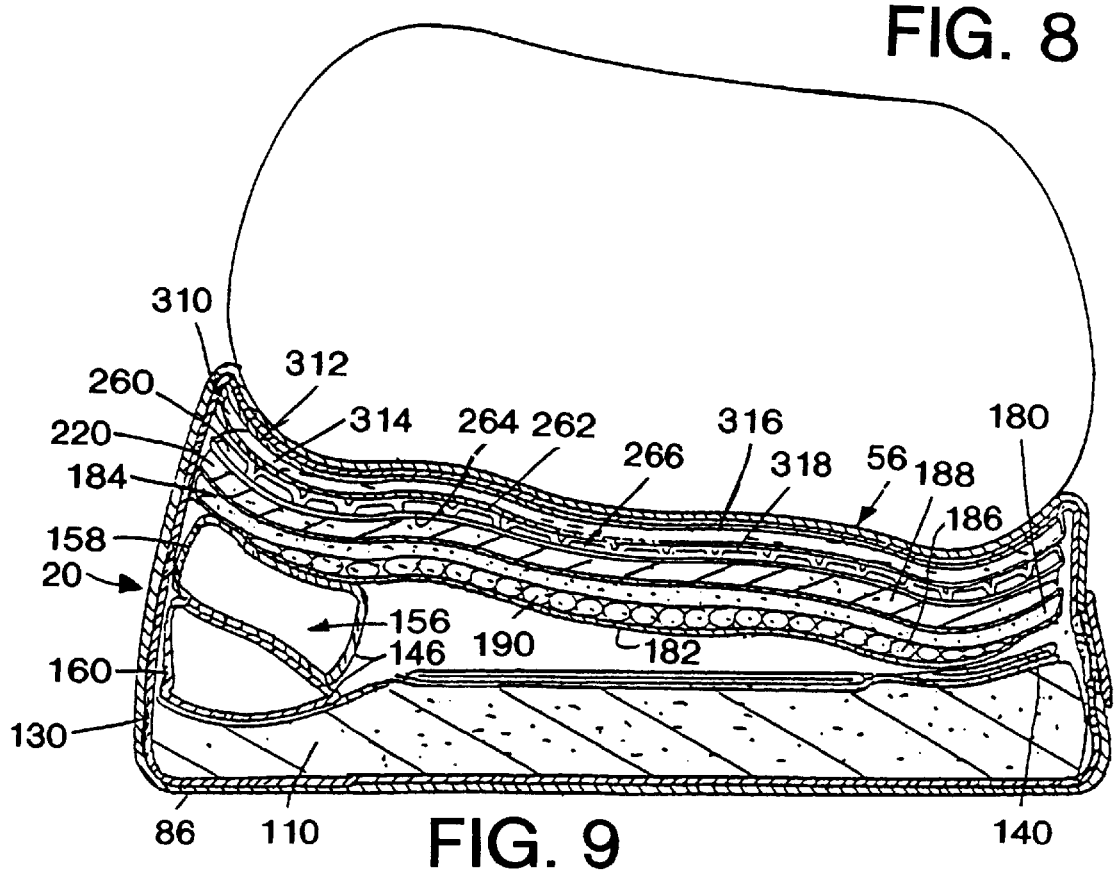
FIG. 9 is a view similar to FIG. 8 showing a double bladder on one side of the patient that is inflated to tilt the patient away from the double bladder, the vacuum bead bag causing the patient-support surface to conform to the shape of the patient, gripping the patient to prevent sliding of the patient when the patient-support surface is tilted.

Once the temperature of patient-support surface 56 and of the patient have reached the desired temperature, the surgical procedure may begin. If desired, surface pad system 20 may be manipulated to reposition the anesthetized patient after the surgical procedure has started. For example, when performing a Cesarean section, it is a common practice for the surgical team to place a roll, a wedge, or some other object under the left hip of the mother to shift the weight of the baby by moving the mother onto her right side. Rather than having members of the surgical team manually reposition the mother, surface pad system 20 in accordance with the present invention can include a second side bladder 158 positioned to lie on top of a first side bladder 160, both of which are appended to bladder pad 140 as shown in FIG. 9. When the surgical team wishes to reposition the mother, a member of the surgical team may simply provide a user input from keypad 378 to controller 370 which will activate the source of pressurized fluid as well as valving of valve manifold 384 necessary to direct the pressurized fluid to first and second side bladders 158, 160 to inflate side bladders 158, 160 as shown in FIG. 9.

Inflation of both side bladders 158, 160 operates to roll the patient to one side as shown in FIG. 9. It will be appreciated by those skilled in the art that using surface pad system 20 in accordance with the present invention to reposition the patient is advantageous for the patient in that a more controlled repositioning can occur than when members of the surgical team manually reposition the patient. In addition, patient-support surface 56 grips the patient to firmly hold the patient in place relative to patient-support surface 56 and to prevent slipping of the patient with respect thereto during repositioning of the patient and patient-support surface 56. Once the baby is removed from the mother, first and second side bladders 158, 160 may easily be deflated to reposition patient-support surface 56 to the generally horizonal position shown in FIG. 8.

Figure 10:
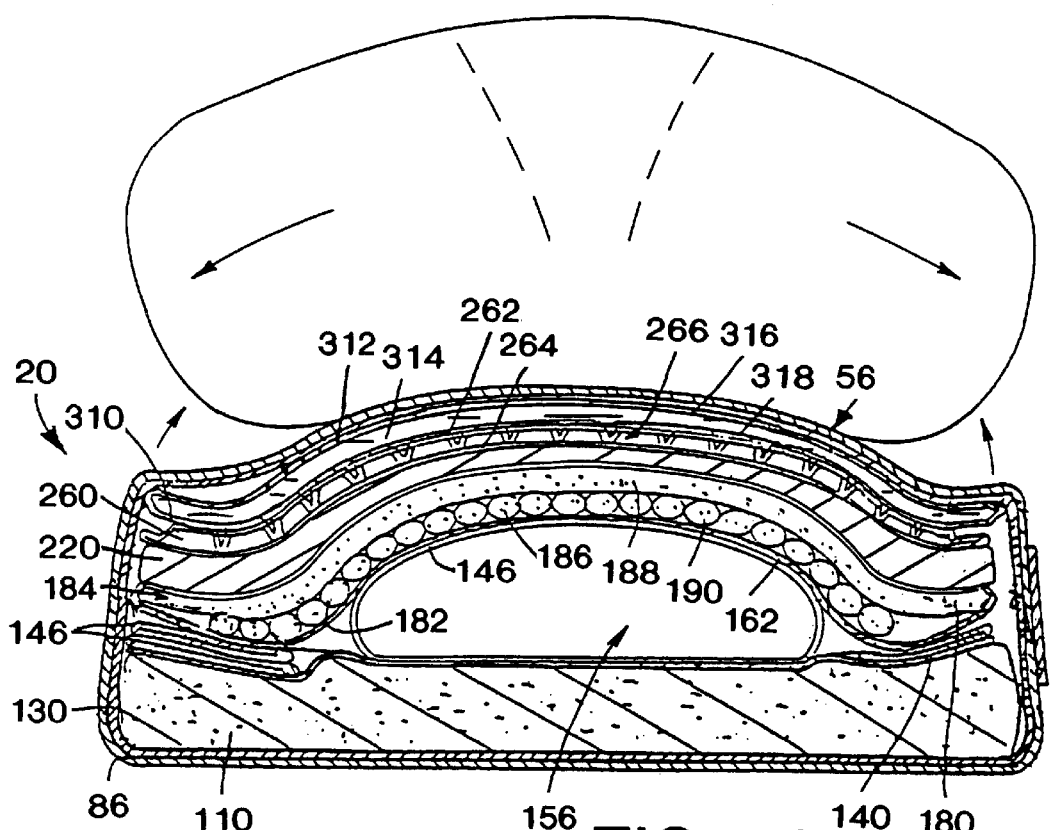
FIG. 10 is a view similar to FIG. 6 showing a central bladder on the bladder pad which is inflated to hyperextend the chest cavity of the patient.
Figure 12:
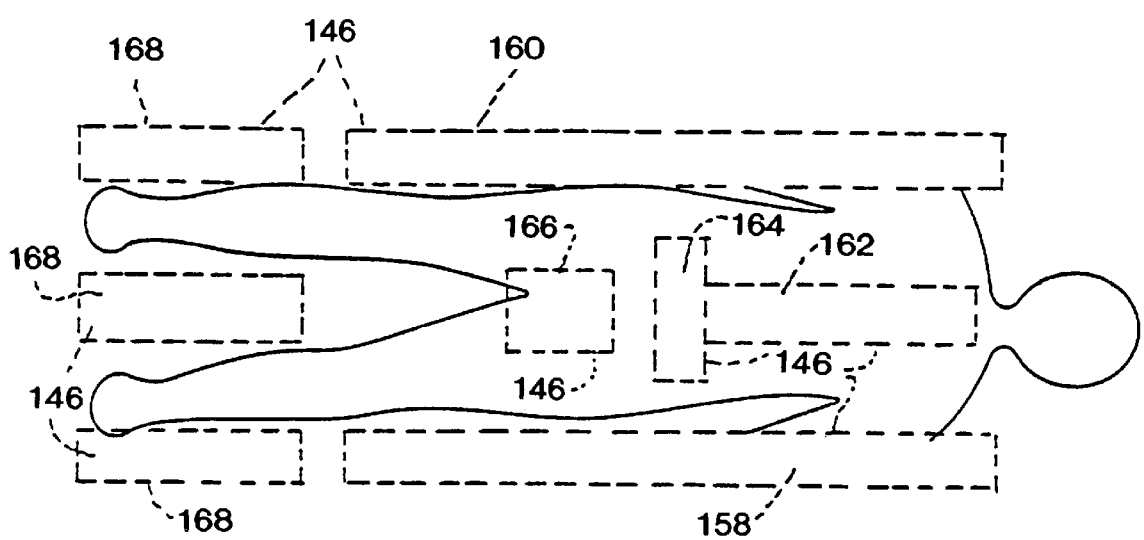
FIG. 12 is a diagrammatic view of a patient lying on the patient-support surface showing the positions of the ladders (in phantom) of illustrative surface pad system beneath the patient.

In preferred embodiments, bladder pad 140 also includes a central support bladder 162 extending longitudinally beneath the spine of the patient on patient-support surface 56 as shown best in FIGS. 10 and 12. Central support bladder 162 can be inflated to a first pressure as shown in FIG. 6 to press patient-support surface 56 against the patient to fill gaps 350 between the patient and patient-support surface 56 as described above. In addition, central support bladder 162 can be inflated to a second pressure which is greater than the first pressure to inflate central support bladder 162 sufficiently to press the spine of the patient upwardly and hyperextend the chest of the patient as shown in FIG. 10. It will be appreciated by those skilled in the art that use of surface pad system 20 to hyperextend the chest cavity of the patient on patient-support surface 56 for certain surgical procedures such as cardiovascular procedures is preferable to the current practice of placing a wedge, a rolled-up gel pack, a rolled-up towel, or other object beneath the anesthetized patient during the procedure. In addition, once the procedure is complete, rather than having to remove the object from underneath the anesthetized patient, use of surface pad system 20 allows for a more controlled lowering of the patient by simply deflating central support bladder 162.

Figure 11:
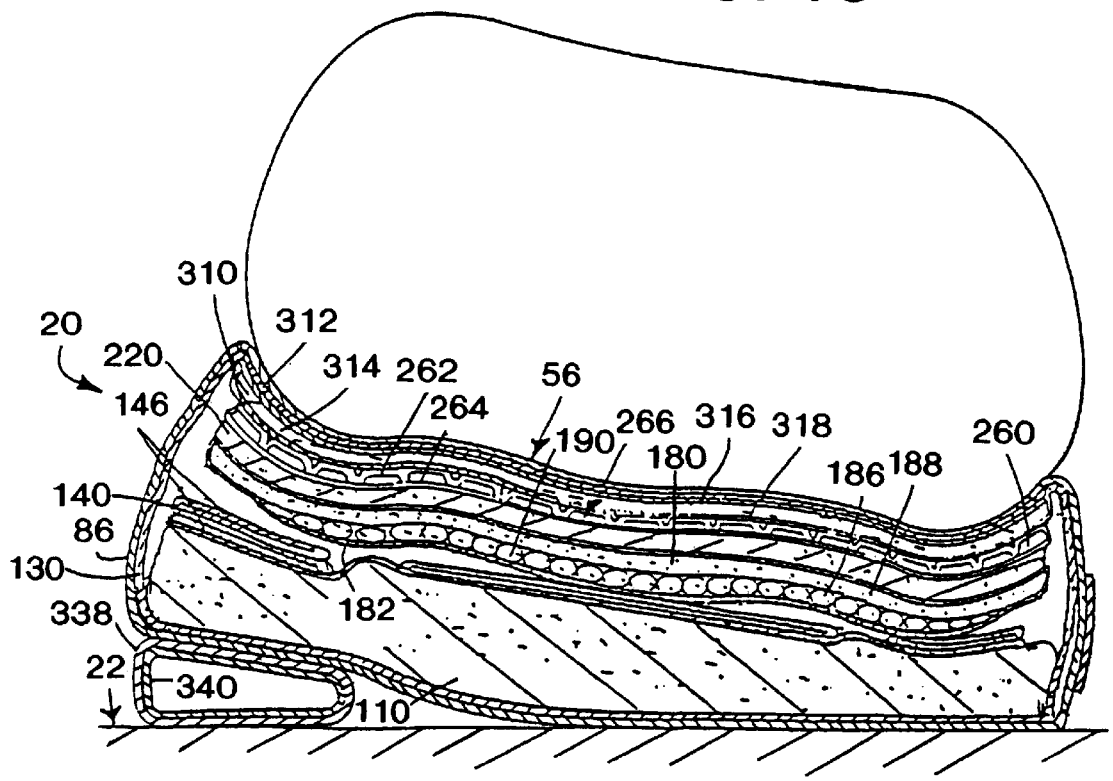
FIG. 11 is a view similar to FIG. 6 showing a pocket formed on a bottom surface of the cover and receiving a separate bladder that is not part of the bladder pad and that can be inflated to tilt the pad section and the patient-support surface.

Cover 86 can be formed to include first and second spaced-apart elongated pockets 338 positioned to lie adjacent to first side 38 of body pad section 34 and second side 40 of body pad section 34, respectively, as shown in FIG. 11. Pockets 338 can each contain bladders 340 which are not connected to bladder pad 140, but which can be inflated to tilt patient-support surface 56 as shown in FIG. 11. It is advantageous in certain surgical procedures to tilt table-top 22 of the surgical table. Bladders 340 are particularly useful during such procedures for "fine-tuning" the orientation of patient-support surface 56.

Illustrative and preferred surface pad system 20 includes pad sections 30 containing bladder pads 140 having bladders 146 that are preferably configured and positioned to lie as shown in FIG. 12 (in phantom) relative to the patient on patient-support surface 56. As described above, surface pad system 20 includes first side bladders 160 positioned to lie on both sides of the patient, at least one second side bladder 158 positioned to lie above one of first side bladders 160, and central support bladder 162 supporting the spine of the patient. In addition, bladders 146 include a lumbar bladder 164 supporting the lumbar region of the patient's back, a sacrum bladder 166 supporting the sacrum of the patient, and three leg-support bladders 168, one of which is positioned to lie between the legs of the patient and the others of which are positioned to lie on the outsides of the legs of the patient.

Although illustrative and preferred surface pad system 20 includes side bladders 158, 160, central support bladder 162, lumbar bladder 164, sacrum bladder 166, and leg support bladders 168 as described above with reference to FIG. 12, the shapes and portions of bladders 146 within surface pad system 20 relative to the patient can be varied without exceeding the scope of the invention as presently perceived. For example, bladders 146 can include a generally "doughnut-shaped" bladder for supporting the head of the patient, the bladder being ring-shaped with an opening formed therein so that the lowermost portion of the head of the patient is adjacent to the opening to minimize the interface pressure against the patient's head as well as to stabilize the patient's head.

Figure 13A:
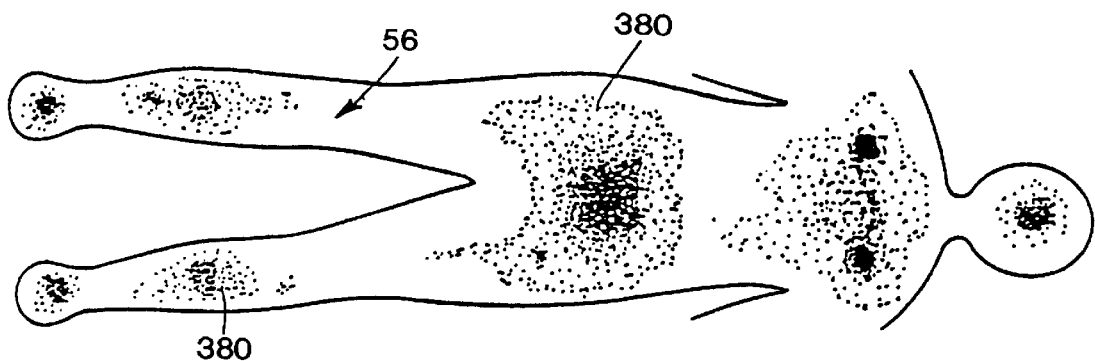
FIG. 13a is a diagrammatic view illustrating the uneven interface pressure distribution of a patient resting on a conventional surface cover for a surgical table.
Figure 13B:
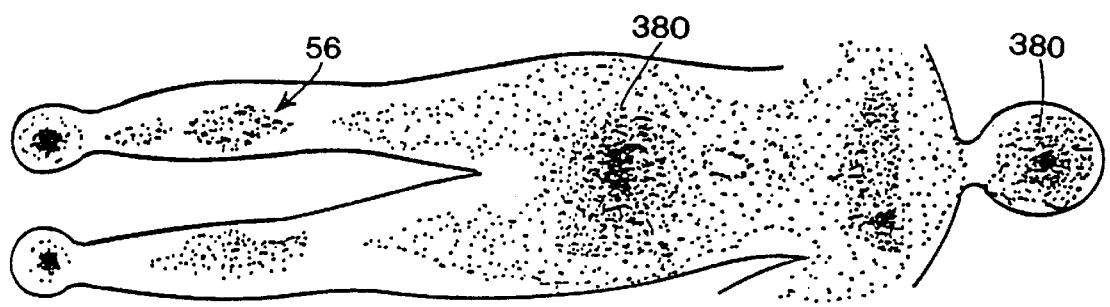
FIG. 13b is a diagrammatic view similar to FIG. 13a illustrating the interface pressure distribution of a patient resting on the patient-support surface of the surface pad system in accordance with the present invention before any of the bladders are inflated and before air is evacuated from the vacuum bead bag.
Figure 13C:
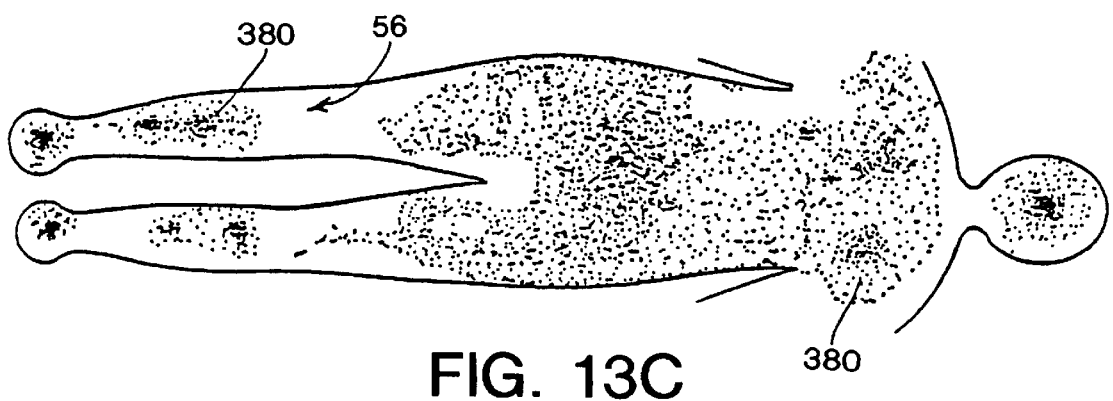
FIG. 13c is a diagrammatic view similar to FIG. 13b showing the interface pressure distribution between the patient and the patient-support surface of the surface pad system in accordance with the present invention after the bladders have been inflated to cause the patient-support surface to conform to the shape of the patient maximizing the surface area of contact between the patient and the patient-support surface and after air has been evacuated from the vacuum bean bags so that the weight of the patient is distributed more evenly over the patient-support surface, thereby minimizing high interface pressure points.

Use of surface pad system 20 in accordance with the present invention minimizes the interface pressure of the high interface pressure points between the patient and patient-support surface 56 as shown diagrammatically in FIGS. 13*a*, 13*b*, and 13*c*. Each of FIGS. 13*a*, 13*b* and 13*c* are diagrammatic representations indicating the interface pressure between the patient and patient-support surface 56. Each diagram includes dots 380 the density of which indicates the magnitude of the interface pressure between the patient and patient-support surface 56. Portions in each of FIGS. 13*a*, 13*b*, and 13*c* showing a high density of dots 380 indicate high interface pressures between the patient and patient-support surface 56 on those portions of patient-support surface 56. Likewise, portions of FIGS. 13*a*, 13*b*, and 13*c* showing a low density of dots 380 or no dots 380 indicates low interface pressures between the patient and patient-support surface 56 or even no interface pressure therebetween indicating that the patient does not engage those portions of patient-support surface 56.

The weight of a patient supported on a conventional surface cover for a surgical table is supported primarily by the head, shoulder blades, sacrum, and heels of the patient as shown diagrammatically in FIG. 13*a*. The above-noted portions of the patient are the downwardly extending extremities of the patient when resting on a conventional surface cover for a surgical table and, as a result, these extremities of the patient support most of the weight of the patient and experience the highest interface pressure between the patient and patient-support surface 56. It can also be seen in FIG. 13*a* that several portions of the patient have low interface pressures against patient-support surface 56 and even no contact with patient-support surface 56 as indicated by portions of FIG. 13*a* having no dots 380 associated therewith. Thus, it can be seen that the weight of the patient is not evenly distributed across the conventional surface cover for a surgical table.

When the patient rests on patient-support surface 56 of surface pad system 20 in accordance with the present invention as shown in FIG. 5 before bladders 146 are inflated and before air is evacuated from interior region 184 of vacuum bead bag 180, high density foam layer 110 and pressure reduction foam layer 220, both of which are made of thermally active visco-elastic foam, cooperate with gel pack 310 to distribute the weight of the patient across patient-support surface 56 as shown diagrammatically in FIG. 13*b*. As can be seen, the high density of dots near the patient's head, shoulder blades, sacrum, and heels indicate that although the weight of the patient is more evenly distributed across patient-support surface 56 than is distributed with the conventional surface covering for a surgical table shown in FIG. 13*a*, there are still some relatively high interface pressure points between the patient and patient-support surface 56.

As indicated above with respect to FIG. 6, inflating bladders 146 causes patient-support surface 56 to conformingly engage the patient and to maximize the surface area of engagement between the patient and patient-support surface 56, thereby minimizing the occurrence of high interface pressure points between the patient and patient-support surface 56 as shown diagrammatically in FIG. 13*c*. By minimizing these high interface pressure points between the patient and patient-support surface 56, use of surface pad system 20 in accordance with the present invention minimizes pressure ulcers, neuropathy, and other nerve disorders and damage to nerve bundles that can result from prolonged exposure to high interface pressures.

In addition, as described above, surface pad system 20 allows the surgical team to manipulate and adjust the temperature of patient-support surface 56 and thus of the patient. The use of bladders 146 to press patient-support surface 56 into conforming engagement with the patient and the placement of thermal pad 260 above bladder pad 140 so that thermal pad is likewise pressed upwardly toward the patient, operates to maximize the heat transfer between thermal pad 260 and the patient through gel pack 310 and top 96 of cover 86.

Surface pad system 20 also allows for an automated and controlled positioning of the patient relative to table-top 22 of-the surgical table while enhancing the stability of the patient during repositioning operations. Instead of having members of the surgical team manually repositioning the anesthetized patient and simultaneously trying to bolster the patient in the new position using wedges, pillows, or other objects that are shoved between the patient and the tops of conventional coverings, surface pad system 20 automatically and controllably repositions the patient when instructed to do so by a member of the surgical team simply by inflating or deflating bladders 146 as required. Use of internal bladders 146 to reposition the patient eliminates the need to use rolled-up towels, pillows, or other objects to support the patient in the new position. These objects, which are placed between the patient and patient-support surface 56, are typically thermal insulators, so that elimination of the use of these objects eliminates an impediment to the heat transfer between patient-support surface 56 and the patient.

As described above, surface pad system 20 in accordance with the present invention includes control housing 74 which contains the controller 370, the heat exchanger 372, the pressurized fluid source 374, vacuum source 376, and a valve manifold 384 as shown diagrammatically in FIG. 14. Controller 370 receives the user input signals from key pad 378 and the temperature input signal as described above from thermocouple 382 positioned in gel pack 310 of body pad section 34. In addition, controller 370 receives temperature input signals from thermocouples 382 positioned in gel packs 310 of each pad section 30 that include thermal pads 260. Controller 370 receives the user input signals and the temperature input signals and provides a heat exchange output signal to heat exchanger 372, a vacuum output signal to vacuum source 376, a pressurized fluid output signal to the pressurized fluid source 374, and a valve positioning signal to valve manifold 384 in response thereto.

Heat exchanger 372 operates to heat and cool the circulating thermoregulation fluid in response to the heat exchanger output signal in order to maintain the temperature of thermocouples 382 at the desired temperature. In preferred embodiments, channels 266 of thermal pads 260 of all pad sections 30 are coupled together and are in fluid communication with one another through thermoregulation fluid supply conduit 62 and thermoregulation fluid return conduit 64. Thus, thermoregulation fluid flows from heat exchanger 372, through each pad section 30 in series, then back to heat exchanger 372. Consequently, one heat exchanger 372 can control the temperature of thermal pads 260 of each pad section 30.

Vacuum source 376 operates to evacuate the atmosphere from interior region 184 of vacuum bead bags 180 or to allow air or another generally inert gas to flow into interior region 184 of vacuum bead bag 80 through conduits 68 in response to the vacuum output signal from controller 370. In preferred embodiments, interior regions 184 of vacuum bead bags 180 of all pad sections 30 are coupled together and are in fluid communication with one another through vacuum conduit 68. Thus, when air is evacuated from conduit 68, air flows from each interior region 184, through conduit 68, to vacuum source 376 forcing compressible beads 194 to squeeze against each other and deform, thereby becoming immobile with respect to one another and forcing vacuum bead bag 180 to its rigid condition. Likewise, when air is permitted to return to interior regions 184, the air flows from vacuum source 376, through conduit 68, to interior regions 184 allowing vacuum bead bags 180 to once again become pliable.

Pressurized fluid source 374 operates to supply pressurized fluid to selected bladders 146 at a pressure in accordance with the pressurized output signal and the valve positioning signal from controller 370 or to allow pressurized fluid to escape from selected bladders 146 in response to the pressurized fluid output signal and the valve positioning signal from controller 370. In preferred embodiments, valve manifold 384 includes a plurality of valves (not shown), including a valve (not shown) associated with each pressurized fluid conduit 60 which is associated with each bladder 146. When a user input signal requires one of the bladders 146 to inflate, pressurized fluid source 374 provides pressurized fluid to valve manifold 384 and the valve associated with the selected bladder 146 opens so that pressurized fluid can flow along conduit 66 associated with the selected bladder 146 to fill and inflate the selected bladder 146. When a user input signal requires one of the bladders 146 to deflate, pressurized fluid is removed from valve manifold 384 and the valve associated with the selected bladder opens so that pressurized fluid can flow along conduit 66 associated with the selected bladder 146 from the selected bladder 146 to valve manifold 384, thereby allowing the selected bladder 146 to deflate.

It will be appreciated by those skilled in the art that use of valve manifold 384 allows surface pad system 20 to include only one source of pressurized fluid 374 to service all bladders 146 rather than requiring a separate source of pressurized fluid for each bladder 146. As mentioned above, the preferred pressurized fluid is air, although any generally inert fluid such as nitrogen, water, or any other suitable liquid or gas can be used as the pressurized fluid to inflate bladders 146. It is therefore within the scope of the invention as presently perceived for the source of pressurized fluid to include an air or water tank, an air compressor, a "house" compressed air or other compressed gas line, a water line of a hospital or other facility, or any other suitable source of pressurized fluid.

Having each of vacuum bead bag 180, bladders 146, and thermal pad 260 controlled by controller 370 provides a convenient single source of information for data logging parameters such as the amount of time a patient spends in a single position, the amount of time a patient spends on surface pad system 20 and thus on table-top 22 of the surgical table, the amount of time the patient spends at a particular temperature, and other parameters related to the operation of surface pad system 20. In addition, controller 370 can coordinate the operation of bladders 146, vacuum bead bag 180, and thermal pad 260, for example, to control the sequence of operations such as providing that bladders 146 inflate before air is evacuated from interior region 184 of vacuum bead bag 180, providing that the air is evacuated from bladders 146 before the temperature of the patient is reduced for surgery, as well as providing computer control for such tasks as controlling the temperature of the patient and patient-support surface 56 for surgical procedures performed at reduced temperatures. If desired, controller 370 can also be programmed to automatically adjust bladders 146, vacuum bead bag 180, and thermal pad 260.

Although illustrative surface pad system 20 includes head pad section 32, body pad section 34, leg pad section 36, first arm pad section 42, and second arm pad section 44, the number of pad sections 30 and the arrangement of pad sections 30 can be varied without exceeding the scope of the invention as presently perceived. For example, head pad section 32 can be eliminated from surface pad system 20 and can be replaced with a conventional head pad for a surgical surface such as a "doughnut-shaped" pad commonly used to support the head of a patient. For another example, if desired, surface pad system 20 can include an additional pad section (not shown) that is positioned to lie between body pad section 34 and leg pad section 36.

In illustrative and preferred surface pad system 20, pad sections 30 are removably coupled to one another so that each pad section 30 can operate independently of the other pad sections 30. Conduits 60 are provided with quick disconnect couplings 72 as shown in FIG. 1 to facilitate disconnecting one of pad sections 30 from another of pad sections 30 and reconnecting to yet another of pad sections or to couplings 62 of hose 76. For example, surface pad system 20 can be operated using body pad section 34, leg pad section 36, and arm pad sections 42, 44, having the head of the patient resting on a conventional pillow. For another example, surface pad system 20 can be operated using only body pad section 34 and leg pad section 36 with the head-of the patient supported by a conventional pillow and the arms of the patient resting on table-top 22 or on top of the patient. As can be seen, the specific configuration or number of pad sections 30 of surface pad system 20 can be varied without exceeding the scope of the invention as presently perceived.

Although the invention has been described in detail with reference to a preferred embodiment, additional variations and modifications exist within the scope and spirit of the invention as described and defined in the following claims.

We claim:

1. A surface pad system for a surgical table, the surface pad system comprising a cover having an upwardly-facing patient-support surface defining an interior region of the surface pad system, a vacuum bead bag received in the interior region, the vacuum bead bag including a flexible cover defining an interior region containing compressible beads, a bladder received in the interior region of the cover and positioned to lie beneath the vacuum bead bag, the bladder defining an interior region and being inflatable when pressurized fluid is received in the interior region of the bladder so that the vacuum bead bag conformingly engages the patient on the patient-support surface when the bladder is inflated, and a layer of foam received in the interior region adjacent to one of the vacuum bead bag and the bladder.

2. The surface pad system of claim 1, wherein the vacuum bead bag includes a lower layer of compressible beads and an upper layer of compressible bead separated from the lower layer of compressible beads by a membrane made from a flexible material.

3. The surface pad system of claim 1, further comprising a bladder pad received in the interior region and including a top wall having an upper surface, a bottom wall and a fluid inlet port in fluid communication with a source of compressed fluid, the bladder being appended to the upper surface, and the bottom wall being formed to include a channel in fluid communication with the bladder and with the fluid inlet port so that fluid can be communicated from the source of compressed fluid to the bladder through the fluid inlet port and the channel to inflate the bladder.

4. The surface pad system of claim 1, further comprising a thermal pad received in the interior region, the thermal pad including means for selecting and maintaining the temperature of the patient-support surface and being positioned to lie above the vacuum bead bag and the bladder.

5. The surface pad system of claim 1, wherein the bladder is positioned to lie beneath the patient-support surface supporting the patient between the shoulder blades of the patient to minimize interface pressure between the shoulder blades of the patient and the patient-support surface when the bladder is inflated to a first pressure.

6. The surface pad system of claim 5, wherein the bladder can be inflated to a second pressure which is greater than the first pressure and the bladder lifts the patient-support surface adjacent to the bladder sufficiently to hyperextend the chest of the patient when the bladder is inflated to the second pressure.

7. The surface pad system of claim 1, wherein the bladder is an elongated longitudinally extending first bladder positioned to lie beneath the patient-support surface supporting the patient between the lower legs of the patient and further comprising elongated and longitudinally extending second and third bladders transversely spaced apart from each other and spaced apart from the first bladder, the first bladder being positioned to lie between the second and third bladders so that the first bladder cooperates with the second and third bladders to cradle the calves and heels of the patient when the first, second, and third bladders are inflated.

8. The surface pad system of claim 1, wherein the bladder is positioned to lie beneath the patient-support surface supporting the sacral area of the patient to minimize the interface pressure between the sacrum of the patient and the patient-support surface.

9. The surface pad system of claim 1, wherein the bladder is positioned to lie beneath the patient-support surface supporting the lumbar area of the patient to minimize the interface pressure between the patient-support surface and the upper back and sacrum of the patient.

10. The surface pad system of claim 1, further comprising a vacuum source, a controller coupled to the vacuum source for controlling the pressure in the interior region of the vacuum bead bag and a source of pressurized fluid in fluid communication with the bladder, the controller being coupled to the source of pressurized fluid for controlling the pressure in the interior region of the bladder so that the controller can coordinate the operation of the vacuum bead bag and the bladder.

11. A surface pad system for a surgical table, the surface pad system comprising:

a cover having an upwardly-facing patient-support surface defining an interior region of the surface pad system, a vacuum bead bag received in the interior region, the vacuum bead bag including a flexible cover defining an interior region containing compressible beads, the vacuum bead bag including a lower layer of compressible beads and an upper layer of compressible bead separated from the lower layer of compressible beads by a membrane made from a flexible material, the membrane being formed to include a plurality of elongated tubes, each tube defining an interior region receiving compressible beads, each layer including a plurality of abutting parallel tubes, and a bladder received in the interior region of the cover and positioned to lie beneath the vacuum bead bag, the bladder defining an interior region and being inflatable when pressurized fluid is received in the interior region of the bladder so that the vacuum bead bag conformingly engages the patient on the patient-support surface when the bladder is inflated.

12. The surface pad system of claim 11, wherein the tubes comprising the upper layer extend in a transverse direction and the tubes comprising the lower layer extend in a longitudinal direction.

13. The surface pad system of claim 11, wherein the tubes comprising the upper layer extend in a longitudinal direction and the tubes comprising the lower layer extend in a transverse direction.

14. A surface pad system for a surgical table, the surface pad system comprising:

a cover having an upwardly-facing patient-support surface defining an interior region of the surface pad system, a vacuum bead bag received in the interior region, the vacuum bead bag including a flexible cover defining an interior region containing compressible beads, a bladder received in the interior region of the cover and positioned to lie beneath the vacuum bead bag, the bladder defining an interior region and being inflatable when pressurized fluid is received in the interior region of the bladder so that the vacuum bead bag conformingly engages the patient on the patient-support surface when the bladder is inflated, a vacuum source, a controller coupled to the vacuum source for controlling the pressure in the interior region of the vacuum bead bag, a source of pressurized fluid in fluid communication with the bladder, the controller being coupled to the source of pressurized fluid for controlling the pressure in the interior region of the bladder so that the controller can coordinate the operation of the vacuum bead bag and the bladder, a thermal pad received in the interior region of the cover, and a heat exchanger coupled to the thermal pad, the thermal pad including a channel in fluid communication with the heat exchanger and receiving thermoregulation fluid therefrom, the controller being coupled to the heat exchanger to control the temperature of the thermoregulation fluid, thus controlling the temperature of the patient-support surface.

15. The surface pad system of claim 14, further comprising a gel layer received in the interior region and positioned to lie on top of the vacuum bead bag, the gel layer including a casing defining an interior region containing a viscous fluid, and a temperature sensor received in the interior region of the gel layer and coupled to the controller for providing an input signal to the controller in response to the temperature of the gel layer, the controller providing an output signal to the heat exchanger in response to the input signal, the heat exchanger controlling the temperature of the thermoregulation fluid in response to the output signal.

16. A surface pad system for a surgical table, the surface pad system comprising a body pad section having a head end, a foot end, and first and second spaced-apart sides therebetween, the body pad section being positioned to lie beneath the torso of the patient, the body pad section including a pad core and an outer cover defining an interior region receiving the pad core, the outer cover having a top and a bottom spaced-apart from the top and positioned to lie beneath the pad core, and an elongated bladder attached to a portion of the bottom of the cover and positioned to lie outside of the interior region of the outer cover between the body pad section and the surgical table, the bladder being positioned to lie adjacent to the first side of the body pad section and being inflatable between a deflated position in which the portion of the bottom of the cover to which the bladder is attached is adjacent to the surgical table and an inflated position in which the portion of the bottom of the cover to which the bladder is attached is lifted above the surgical table so that the body pad section is tilted relative to the surgical table when the bladder is inflated.

17. The surface pad system of claim 16, wherein the bottom of the cover includes first and second spaced-apart longitudinal sides and the cover is formed to include a pocket positioned to lie adjacent to the first side beneath the bottom of the cover, elongated bladder being positioned in the pocket.

18. A surface pad system for a surgical table, the surface pad system comprising a cover defining an interior region, a top having an upwardly-facing patient-support surface, and a bottom having a downwardly-facing bottom surface spaced apart from the patient-support surface, a high density foam first support layer received in the interior region and engaging the bottom of the cover, a bladder received in the interior region and engaging the first support layer, a lower layer of positioning beads received in the interior region and engaging the bladder, the lower layer of positioning beads including a plurality of transversely extending elongated tubes made from a flexible material, each tube defining an interior region receiving beads, an upper layer of positioning beads received in the interior region and engaging the lower layer of positioning beads, the upper layer of positioning beads including a plurality of longitudinally extending elongated tubes made from a flexible material, each tube defining an interior region receiving beads, a high density foam second support layer received in the interior region and engaging the upper layer of positioning beads, a thermal pad received in the interior region and engaging the second support layer, the thermal pad including a casing defining a serpentine channel receiving a thermoregulation fluid at a selected temperature, a gel layer received in the interior region and engaging the thermal pad, the gel layer including a casing defining an interior region containing a viscous fluid, and a cut-proof material layered between the gel layer and the top of the cover to prevent the penetration of the gel layer by objects that penetrate the top of the cover.

19. The surface pad system of claim 18, wherein the bottom of the cover includes first and second spaced-apart longitudinal sides and the cover is formed to include a pocket positioned to lie adjacent to the first side beneath the bottom of the cover, the pocket defining a pocket interior, and further comprising a bladder received by the pocket, the bladder being inflatable and deflatable to move the operating surface from a generally horizontal position when the bladder is deflated to a tilted position when the bladder is inflated.

20. The surface pad system of claim 18, further comprising a heat exchanger regulating the temperature of thermoregulation fluid provided to the channel of the thermal pad, a vacuum source for evacuating air from the upper and lower layers of positioning beads, a pressurized air source for providing pressurized fluid to the bladder, and a controller for controlling and coordinating the operation of the heat exchanger, the vacuum source, and the pressurized fluid source.

21. The surface pad system of claim 18, wherein the cover is made from a bi-directional stretch material that is stretchable both transversely and longitudinally so that the cover stretches instead of folding when the cover moves.

22. A vacuum bead bag for use in a surface pad system for a surgical table, the vacuum bead bag comprising a casing having an interior region, a plurality of elongated flexible tubes received in the interior region of the casing, each tube defining an interior region of the tube, and a plurality of compressible beads, each tube receiving beads of the plurality of compressible beads in the interior region of each tube, wherein a first set of tubes of the plurality of tubes includes tubes extending in a first direction and a second set of tubes of the plurality of tubes is positioned to lie above the first set of tubes, the second set of tubes including tubes extending in a second direction, the second direction being generally perpendicular to the first direction.

23. A bladder pad for use in a surface pad system for a surgical table, the bladder pad comprising:

a sheet having a first surface facing a first direction and a second surface facing a second direction which is opposite the first direction, the sheet being formed to include an opening extending therethrough, a bladder appended to the first surface and being formed to include an interior region and an opening in fluid communication with both the interior region of the bladder and the opening formed in the sheet, and a second sheet appended to the second surface of the first sheet and cooperating therewith to define a channel for receiving pressurized fluid, the channel being formed to include an opening in fluid communication with the opening of the sheet so that the channel is in fluid communication with the interior region of the bladder.

24. A surface pad system for a surgical table, the surface pad system comprising a cover defining an interior region and including an upwardly-facing top and a bottom, and a pad core received in the interior region of the cover, the pad core including a base layer received in the interior region and engaging the bottom of the cover, a bladder received in the interior region and engaging the base layer, a layer of positioning beads received in the interior region above the bladder, and at least one additional support element including at least one of a high density foam support layer, a thermal pad, a gel layer, and a cut-proof material layer located in the interior region above the layer of positioning beads.

25. The surface pad system of claim 24, wherein the bladder is inflatable to a first pressure to adjust the support and firmness characteristics of the surface pad system adjacent to the bladder so that the interface pressure of high interface pressure points between the patient and the patient-support surface is minimized.

26. The surface pad system of claim 25, wherein the bladder is inflatable to a second pressure to adjust the position of the patient.

27. The surface pad system of claim 24, wherein the layer of positioning beads includes a lower layer of positioning beads received in the interior region and engaging the bladder, the lower layer of positioning beads including a plurality of transversely extending elongated tubes made from a flexible material, each tube defining an interior region receiving beads, and an upper layer of positioning beads received in the interior region and engaging the lower layer of positioning beads, the upper layer of positioning beads including a plurality of longitudinally extending elongated tubes made from a flexible material, each tube defining an interior region receiving beads.

28. The surface pad system of claim 24, wherein the bottom of the cover includes first and second spaced-apart longitudinal sides and the cover is formed to include a pocket positioned to lie adjacent to the first side beneath the bottom of the cover, the pocket defining a pocket interior, and further comprising a bladder received by the pocket, the bladder being inflatable and deflatable to move the operating surface from a generally horizontal position when the bladder is deflated to a tilted position when the bladder is inflated.

* * * * *